(12) United States Patent
Brun et al.

(10) Patent No.: US 7,806,941 B2
(45) Date of Patent: Oct. 5, 2010

(54) COSMETIC COMPOSITION COMPRISING AT LEAST ONE ORGANOSILICON COMPOUND COMPRISING AT LEAST ONE BASIC FUNCTION, AT LEAST ONE HYDROPHOBIC FILM-FORMING POLYMER, AT LEAST ONE PIGMENT AND AT LEAST ONE VOLATILE SOLVENT

(75) Inventors: Gaëlle Brun, Paris (FR); Arnaud Bonnamy, Versailles (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/569,287

(22) Filed: Sep. 29, 2009

(65) Prior Publication Data

US 2010/0083446 A1    Apr. 8, 2010

Related U.S. Application Data

(60) Provisional application No. 61/103,714, filed on Oct. 8, 2008, provisional application No. 61/103,718, filed on Oct. 8, 2008.

(30) Foreign Application Priority Data

| Sep. 30, 2008 | (FR) | ................................ 08 56597 |
| Sep. 30, 2008 | (FR) | ................................ 08 56598 |

(51) Int. Cl.
  *A61Q 5/10* (2006.01)
(52) U.S. Cl. ................ 8/405; 8/435; 8/552; 8/581; 8/632; 8/637.1; 132/202; 132/208
(58) Field of Classification Search ............. 8/405, 8/435, 552, 581, 632, 637.1; 132/202, 208
  See application file for complete search history.

(56) References Cited

U.S. PATENT DOCUMENTS

| 4,344,763 A | 8/1982 | Tolgyesi et al. |
| 5,281,240 A | 1/1994 | McGee |
| 6,106,577 A | 8/2000 | Audousset et al. |
| 6,352,699 B1 | 3/2002 | Mondet et al. |
| 6,953,572 B1 | 10/2005 | Samain et al. |
| 2004/0013632 A1 | 1/2004 | Giroud et al. |
| 2006/0110351 A1 | 5/2006 | Koehler et al. |
| 2008/0127429 A1 | 6/2008 | Brun et al. |

FOREIGN PATENT DOCUMENTS

| EP | 0 159 628 B1 | 10/1985 |
| EP | 1 767 187 A2 | 3/2007 |
| EP | 1 767 189 A2 | 3/2007 |
| FR | 2 907 678 A1 | 5/2008 |
| FR | 2 922 758 A1 | 5/2009 |
| FR | 2 922 759 A1 | 5/2009 |
| WO | WO 97/18795 | 5/1997 |
| WO | WO 98/44906 | 10/1998 |
| WO | WO 01/22925 A1 | 4/2001 |
| WO | WO 01/74308 A2 | 10/2001 |

OTHER PUBLICATIONS

English abstract of the patent EP 1767187 A2 (2007).*
STIC Search Report dated May 28, 2010.*
French Search Report for FR 0856597, dated May 5, 2009.
French Search Report for FR 0856598, dated May 6, 2009.
English language abstract of EP 1 767 187 A2, Mar. 28, 2007.
English language abstract of EP 1 757 189 A2, Mar. 28, 2007.
English language abstract of FR 2 922 758 A1, May 1, 2009.
English language abstract of FR 2 922 759 A1, May 1, 2009.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a cosmetic composition for treating keratin fibers, for example human keratin fibers such as the hair, comprising, in a cosmetically acceptable medium, at least one organosilicon compound chosen from silanes comprising one, two and three silicon atoms, wherein the at least one organosilicon compound also comprises at least one basic chemical function and at least one group chosen from hydroxyl and hydrolysable groups per molecule; at least one hydrophobic film-forming polymer; at least one pigment; and at least one volatile solvent. The present disclosure also relates to a process for treating keratin fibers, comprising applying to the keratin fibers the compositions according to the present disclosure.

13 Claims, No Drawings

COSMETIC COMPOSITION COMPRISING AT LEAST ONE ORGANOSILICON COMPOUND COMPRISING AT LEAST ONE BASIC FUNCTION, AT LEAST ONE HYDROPHOBIC FILM-FORMING POLYMER, AT LEAST ONE PIGMENT AND AT LEAST ONE VOLATILE SOLVENT

This application claims benefit of U.S. Provisional Application Nos. 61/103,714 and 61/103,718, filed Oct. 8, 2008, the contents of which are incorporated herein by reference. This application also claims benefit of priority under 35 U.S.C. §119 to French Patent Application Nos. FR 0856597 and FR 0856598, filed Sep. 30, 2008, the contents of which are also incorporated herein by reference.

The present disclosure relates to a ready-to-use cosmetic composition for treating keratin fibers, including human keratin fibers such as the hair, comprising at least one specific organosilicon compound, at least one hydrophobic film-forming polymer, at least one pigment and at least one volatile solvent. The disclosure also relates to a cosmetic process for treating keratin fibers and also to a method for making a composition for dyeing keratin fibers.

The present disclosure similarly relates to the use of a cosmetic composition comprising, in a cosmetically acceptable medium, at least one specific organosilicon compound as described herein, as a pretreatment to a composition comprising at least one hydrophobic film-forming polymer, at least one pigment, and at least one volatile solvent.

Hair is generally damaged and embrittled by the action of external atmospheric agents such as light and bad weather, and mechanical or chemical treatments such as blow-drying, combing, bleaching, permanent-waving, and/or dyeing. As a result, the hair may be difficult to manage, such as it may be difficult to disentangle or to style, and a head of hair, even a thick head of hair, can have difficulty in maintaining a pleasant-looking style due to the fact that the hair lacks vigour, body, and liveliness.

This degradation of hair is moreover accentuated by repetition of hair permanent dyeing treatments, which consist in applying to the hair at least one dye precursor and an oxidizing agent.

Thus, to overcome this, it is now common practice to apply styling products that condition the hair while also giving it body, mass, or volume.

These styling products are generally cosmetic haircare compositions comprising at least one polymer that has strong affinity for the hair and that usually has the function of forming a film on the surface of the hair in order to modify its surface properties, for example to condition it or to give it particular optical properties.

One drawback associated with the use of these haircare compositions lies in the fact that the cosmetic effects imparted by such compositions have a tendency to disappear, for example from the first shampoo wash.

Moreover, in the field of dyeing keratin fibers, it is already known practice to dye keratin fibers via various techniques using direct dyes for non-permanent colorations or dye precursors for permanent colorations.

Non-permanent dyeing or direct dyeing consists in dyeing keratin fibers with dye compositions comprising direct dyes. These dyes are colored and coloring molecules that have affinity for keratin fibers. They are applied to the keratin fibers for the time required to obtain the desired coloration, and are then rinsed out.

The standard dyes that are used include, for example, dyes of the nitrobenzene, anthraquinone, nitropyridine, azo, xanthene, acridine, azine, or triarylmethane type, or natural dyes.

Some of these dyes may be used under lightening conditions, which enables the production of colorations that are visible on dark hair.

It is also known practice to dye keratin fibers permanently via oxidation dyeing. This dyeing technique consists in applying to the keratin fibers a composition comprising dye precursors such as oxidation bases and couplers. These precursors, under the action of an oxidizing agent, form at least one colored substance in the hair.

The variety of molecules used as oxidation bases and couplers allows a wide range of colors to be obtained, and the colorations resulting therefrom may be strong and resistant to external agents, such as to light, bad weather, washing, perspiration, and rubbing.

In order to be visible on dark hair, these two dyeing techniques may require prior or simultaneous bleaching of the keratin fibers. This bleaching step, performed with an oxidizing agent such as hydrogen peroxide or persalts, can result in appreciable degradation of the keratin fibers, which impairs their cosmetic properties. The hair then has a tendency to become coarse, more difficult to disentangle, and more brittle.

Another dyeing method consists in using pigments. For example, the use of pigment at the surface of the keratin fibers generally makes it possible to obtain visible colorations on dark hair, since the surface pigment may mask the natural color of the fiber. The use of pigment for dyeing keratin fibers is described, for example, in patent application FR 2 741 530, which discloses using for the temporary dyeing of keratin fibers a composition comprising at least one dispersion of film-forming polymer particles comprising at least one acid function and at least one pigment dispersed in the continuous phase of the dispersion.

The colorations obtained via this dyeing method may have the drawback of being removed from the first shampoo wash.

To overcome these drawbacks, it has been proposed to perform coating by applying to the hair a composition comprising a hydrophobic film-forming polymer, such as a polysiloxane/polyurea block copolymer, in patent application FR 2 907 677. Such a composition may produce well-coated, non-greasy hair. The coatings obtained may show good resistance to shampooing, but may have the drawback of having poor staying power if the hair is sensitized.

There is thus a need to develop cosmetic compositions for treating keratin fibers and for example for dyeing human keratin fibers such as the hair and to use a hair dyeing process that can lead to colored coatings that are at least one of shampoo-fast and resistant to external attacking factors, while at the same time maintaining good cosmetic properties (giving the hair body, mass, or volume), in a long-lasting manner, irrespective of the sensitization of the treated hair.

It has been found that the use of a cosmetic composition for treating keratin fibers, such as human keratin fibers such as the hair, comprising at least one specific organosilicon compound, at least one hydrophobic film-forming polymer, at least one pigment, and at least one volatile solvent can lead to a colored coating that is at least one of shampoo-fast and resistant to external attacking factors, while at the same time maintaining good cosmetic properties, irrespective of the sensitization of the treated hair.

In addition, it has been found that it is possible to use on keratin fibers cosmetic compositions comprising at least one specific organosilicon compound as defined herein as a pretreatment to a cosmetic composition comprising at least one hydrophobic film-forming polymer, at least one pigment, and at least one volatile solvent in order also to obtain a colored hair coating that shows satisfactory fastness with respect to external attacking factors, such as blow-drying, friction, or perspiration.

The coatings thus obtained generally are in the form of a smooth, uniform deposit that shows excellent adhesion to the hair.

Moreover, it has been found that the hairs can remain individualized.

The term "individualized hairs" means hairs which, after application of the composition and drying, are not stuck together (e.g., are separate from each other) and therefore do not form clumps of hair, since the coating is formed around virtually every hair.

Furthermore, it has been found that the application to keratin fibers of a cosmetic composition comprising at least one suitably selected organosilicon compound as a pretreatment to a cosmetic composition comprising at least one hydrophobic film-forming polymer, at least one pigment and at least one volatile solvent can improve the affinity between the keratin fibers and the hydrophobic film-forming polymer/pigment complex, irrespective of the sensitization of the hair.

It has also been observed that the application to keratin fibers of a cosmetic composition comprising at least one suitably selected organosilicon compound as defined herein as a pretreatment to a composition comprising at least one hydrophobic film-forming polymer, at least one pigment and at least one volatile solvent can make it possible to give the hair mass and body that are long-lasting, for example with respect to shampooing.

Moreover, without being bound by theory, when the pretreatment composition comprises water or when it is applied in the presence of water, for example to wet hair, the at least one organosilicon compound can become hydrolysed and then condensed to form a hybrid prepolymer that promotes the adhesion of the at least one organosilane compound to the hair.

It has also been observed that the shampoo-fastness of the coloration is improved compared with that obtained with cosmetic compositions based on hydrophobic film-forming polymers and volatile solvent used alone.

The present disclosure thus relates to a ready-to-use cosmetic composition for treating keratin fibers, for example human keratin fibers such as the hair, comprising:
  at least one organosilicon compound chosen from silanes comprising one, two and three silicon atoms, wherein the at least one organosilicon compound also comprises at least one basic chemical function, and at least one group chosen from hydroxyl and hydrolysable groups per molecule;
  at least one hydrophobic film-forming polymer;
  at least one pigment; and
  at least one volatile solvent.

The present disclosure also relates to a process for treating keratin fibers, comprising applying, to the keratin fibers, a cosmetic composition comprising
  at least one organosilicon compound chosen from silanes comprising one, two and three silicon atoms, wherein the at least one organosilicon compound also comprises at least one basic chemical function and at least one group chosen from hydroxyl and hydrolysable groups per molecule,
  at least one hydrophobic film-forming polymer,
  at least one pigment, and
  at least one volatile solvent; and drying the keratin fibers at a temperature greater than 40° C.

Similarly, the present disclosure relates to the use of the composition according to the disclosure for dyeing keratin fibers, for example human keratin fibers such as the hair.

The present disclosure also relates to a method for making a composition for dyeing keratin fibers comprising combining, in a cosmetically acceptable medium:
  at least one organosilicon compound chosen from silanes comprising one, two and three silicon atoms, wherein the at least one organosilicon compound also comprises at least one basic chemical function and at least one group chosen from hydroxyl and hydrolysable groups per molecule;
  at least one hydrophobic film-forming polymer;
  at least one pigment; and
  at least one volatile solvent
  wherein the ingredients can be added in any order.

Moreover, the present disclosure relates to the use of a cosmetic composition comprising, in a cosmetically acceptable medium, at least one organosilicon compound chosen from silanes comprising one, two or three silicon atoms, the at least one organosilicon compound also comprising at least one basic chemical function and at least one group chosen from hydroxyl and hydrolysable groups per molecule, as a pretreatment to be followed by a cosmetic composition comprising at least one hydrophobic film-forming polymer, at least one pigment and at least one volatile solvent.

Thus, the cosmetic composition comprising the at least one suitably selected organosilicon compound as described herein is used for the pretreatment of the keratin fibers before the application of the cosmetic composition comprising the at least one hydrophobic film-forming polymer, the at least one pigment and the at least one volatile solvent.

The present disclosure thus relates to a process for treating keratin fibers, comprising
  applying to the keratin fibers a cosmetic pretreatment composition comprising, in a cosmetically acceptable medium, at least one organosilicon compound chosen from silanes comprising one, two and three silicon atoms, wherein the at least one organosilicon compound also comprises at least one basic chemical function and at least one group chosen from hydroxyl and hydrolysable groups per molecule, and
  applying to the keratin fibers a cosmetic composition comprising at least one hydrophobic film-forming polymer, at least one pigment, and at least one volatile solvent.

Other subjects and characteristics, aspects and benefits of the present disclosure will emerge more clearly upon reading the description and the non-limiting examples that follow.

The at least one organosilicon compound according to the present disclosure is chosen from organosilanes comprising one, two, and three silicon atoms, for example two silicon atoms. They must also comprise at least one basic chemical function. The at least one basic chemical function may correspond to any function that gives the silicon compound a basic nature, for example an amine function such as a primary, secondary, or tertiary amine function. The at least one basic chemical function of the at least one organosilicon compound according to the disclosure may optionally comprise other functions, for instance another amine function, an acid function, or a halogen function.

The at least one organosilicon compound used according to the disclosure also comprises at least one group chosen from hydrolysable and hydroxyl groups per molecule. The hydrolysable groups can be, for example alkoxy, aryloxy, or halogen groups. They may also optionally comprise other chemical functions such as acid functions.

According to at least one embodiment, the at least one organosilicon compound used according to the disclosure is chosen from the compounds of formula (I)

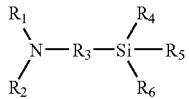
(I)

wherein:
$R_4$ represents a halogen, a group OR', or R'$_1$;
$R_5$ represents a halogen, a group OR'', or R'$_2$;
$R_6$ represents a halogen, a group OR''', or R'$_3$;
$R_1$, $R_2$, $R_3$, R', R'', R''', R'$_1$, R'$_2$, and R'$_3$ represent, independently of each other, a saturated or unsaturated, linear or branched hydrocarbon-based group optionally bearing at least one additional chemical group, wherein $R_1$, $R_2$, R', R'', and R''' also can be hydrogen, and at least two of the groups $R_4$, $R_5$, and $R_6$ are different from the groups R'$_1$, R'$_2$, and R'$_3$.

For example, the groups $R_1$, $R_2$, R', R'$_1$, R'$_2$, R'$_3$, R'', and R''' can be chosen from $C_1$-$C_{12}$ alkyl radicals, $C_5$-$C_{14}$ aryl radicals, ($C_1$-$C_8$)alkyl($C_5$-$C_{14}$)aryl radicals, and ($C_5$-$C_{14}$)aryl($C_1$-$C_8$)alkyl radicals.

For further example, the groups $R_1$, $R_2$, R', R'$_1$, R'$_2$, R'$_3$, R'', and R''' can be chosen from $C_1$-$C_{12}$ alkylene radicals, optionally substituted with an amino group, $C_5$-$C_{14}$ arylene radicals, ($C_1$-$C_8$)alkylene($C_5$-$C_{14}$)arylene radicals, and ($C_5$-$C_{14}$)arylene($C_1$-$C_8$)alkylene radicals.

For example, the group $R_3$ can be chosen from $C_1$-$C_{12}$ alkylene radicals, optionally substituted with an amino group, $C_5$-$C_{14}$ arylene radicals, ($C_1$-$C_8$)alkylene($C_5$-$C_{14}$)arylene radicals and ($C_5$-$C_{14}$)arylene($C_1$-$C_8$)alkylene radicals.

According to at least one embodiment, the at least one organosilicon compound present in the ready-to-use cosmetic composition and in the composition used as a pretreatment according to the disclosure, corresponding to formula (I), is chosen from 3-aminopropyltriethoxysilane, 3-aminopropylmethyldiethoxysilane, N-(2-aminoethyl)-3-aminopropyltriethoxysilane, and 3-(2-aminoethylamino)propylmethyldiethoxysilane.

According to another embodiment, the at least one organosilicon compound present in the ready-to-use cosmetic composition and the composition used as a pretreatment according to the disclosure can be chosen from the compounds of formula (II):

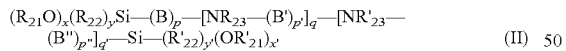
(II)

wherein:
$R_{21}$, $R_{22}$, R'$_{21}$, and R'$_{22}$ each independently represent a saturated or unsaturated, linear or branched hydrocarbon-based chain, optionally containing at least one heteroatom, optionally interrupted or substituted with at least one group chosen from ether, ester, amine, amide, carboxyl, hydroxyl, and carbonyl groups, x is an integer ranging from 1 to 3, y=3−x, x' is an integer ranging from 1 to 3, y'=3−x', p=0 or 1, p'=0 or 1, p''=0 or 1, q=0 or 1, q'=0 or 1, on the condition that at least q or q' is other than zero, B, B', and B'' each independently represent a linear or branched divalent $C_1$-$C_{20}$ alkylene radical, $R_{23}$ and R'$_{23}$ each independently represent a hydrogen atom or a saturated or unsaturated, linear or branched hydrocarbon-based chain, optionally comprising at least one heteroatom, optionally interrupted or substituted with at least one ether, ester of a $C_1$-$C_{20}$ alcohol, amine, carboxyl, alkoxysilane, $C_6$-$C_{30}$ aryl, hydroxyl or carbonyl groups, or a heterocyclic or non-heterocyclic aromatic ring, optionally substituted with at least one ester of a $C_3$-$C_{20}$ alcohol, amine, amide, carboxyl, alkoxysilane, hydroxyl, carbonyl, or acyl group.

As explained previously, $R_{21}$, $R_{22}$, R'$_{21}$, and R'$_{22}$ each independently represent a hydrocarbon-based chain. The term "hydrocarbon-based chain" for example may mean a chain comprising from 1 to 30 and for instance 1 to 10 carbon atoms.

Similarly, $R_{23}$ and R'$_{23}$ may represent a hydrocarbon-based chain. In this case, a chain comprising from 1 to 30 and for example, such as 1 to 10 carbon atoms.

For example, the aromatic ring can comprise from 6 to 30 carbon atoms. For instance, it can also be an optionally substituted phenyl radical.

In at least one embodiment, $R_{21}$=R'$_{21}$; $R_{22}$=R'$_{22}$; x=x'; y=y'; p=p'; A=A'; q=1 and q'=0.

The at least one organosilicon compound of formula (II) may also have the following characteristics, taken alone or in combination:

$R_{21}$, $R_{22}$, R'$_{21}$, and R'$_{22}$, which may be identical or different, represent a $C_1$-$C_4$ alkyl,
p=p'=1,
B and B', which may be identical or different, represent a linear $C_1$-$C_4$ alkylene, and
$R_{23}$ is hydrogen.

For example, the at least one organosilicon compound may comprise a substituent comprising a secondary amine function, for instance bis[3-(triethoxysilyl)propyl]amine of formula $(CH_3CH_2O)_3$—Si$(CH_2)_3$NH$(CH_2)_3$Si$(OCH_2CH_3)_3$ sold by the company Fluorochem, bis[trimethoxysilylpropyl]amine of formula $(CH_3O)_3$—Si$(CH_2)_3$NH—$(CH_2)_3$Si$(OCH_3)_3$ sold by the company Gelest, bis[methyldiethoxysilylpropyl]amine of formula $(CH_3CH_2O)_2CH_3$Si$(CH_2)_3$NH$(CH_2)_3$SiCH$_3(OCH_2CH_3)_2$ sold by the company Gelest, and bis[3-trimethoxysilylpropyl]ethylenediamine of formula $(CH_3O)_3$Si$(CH_2)_3$NH$(CH)_2$NH—$(CH_2)_3$Si$(OCH_3)_3$ sold by the company Gelest. For example, in at least one embodiment, bis[3-(triethoxysilyl)propyl]amine and bis[methyldiethoxysilylpropyl]amine is used.

According to another embodiment of the present disclosure, the at least one organosilicon compound is chosen from the compounds of formula (III):

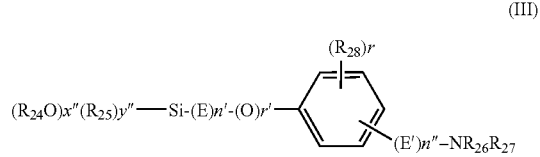
(III)

wherein:
$R_{24}$ and $R_{25}$ each independently represent a saturated or unsaturated, linear or branched hydrocarbon-based chain, optionally containing at least one heteroatom, optionally interrupted or substituted with at least one group chosen from ether, ester, amine, amide, carboxyl, hydroxyl, and carbonyl groups,
x''=2 or 3;
y''=3−x'';
n'=0 or 1;
n''=0 or 1;

E and E' each independently represent a linear or branched divalent $C_1$-$C_{20}$ alkylene radical, $R_{26}$ and $R_{27}$ each independently represent hydrogen or a saturated or unsaturated, linear or branched hydrocarbon-based chain optionally comprising at least one heteroatom, optionally interrupted or substituted with at least one entity chosen from ethers; esters of a $C_1$-$C_{20}$ alcohol, amine, carboxyl, alkoxysilane, $C_6$-$C_{30}$ aryl, hydroxyl or carbonyl groups; and heterocyclic or non-heterocyclic aromatic rings, optionally substituted with at least one ester of a $C_1$-$C_{20}$ alcohol, amine, amide, carboxyl, alkoxysilane, hydroxyl, carbonyl, or acyl groups, r is an integer ranging from 0 to 4, r'=0 or 1, the group(s) $R_{28}$ each independently represent hydrogen or a saturated or unsaturated, linear or branched hydrocarbon-based chain, for example of $C_1$-$C_{10}$, optionally comprising at least one heteroatom, optionally interrupted or substituted with at least one entity chosen from ethers; esters of a $C_1$-$C_{20}$ alcohol, amine, carboxyl, alkoxysilane, $C_6$-$C_{30}$ aryl, hydroxyl or carbonyl groups; and heterocyclic or non-heterocyclic aromatic rings, optionally substituted with at least one ester of a $C_1$-$C_{20}$ alcohol, amine, amide, carboxyl, alkoxysilane, hydroxyl, carbonyl, or acyl groups.

As explained previously, $R_{24}$ and $R_{25}$ each independently represent a hydrocarbon-based chain. The term "hydrocarbon-based chain" for example means a chain containing from 1 to 30 and for instance 1 to 10 carbon atoms.

Similarly, $R_{26}$ and $R_{27}$ may represent a hydrocarbon-based chain. In this case, it can be for example a chain containing from 1 to 30 and for instance 1 to 10 carbon atoms.

For example, the aromatic ring may contain from 6 to 30 carbon atoms. For instance, it can be an optionally substituted phenyl radical.

The at least one organosilicon compound of formula (III) may have the following characteristics, taken alone or in combination:

$R_{24}$ is a $C_1$-$C_4$ alkyl, x''=3, n'=n''=1; r=r'=0, $R_{26}$ and $R_{27}$ independently represent hydrogen or a group chosen from $C_1$-$C_4$ alkyl groups, $C_1$-$C_4$ hydroxyalkyl groups, and $C_1$-$C_4$ aminoalkyl groups.

For instance, the at least one organosilicon compound of formula (III) may be chosen from:

3-(m-aminophenoxy)propyltrimethoxysilane, of formula:

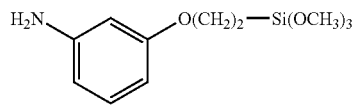

p-aminophenyltrimethoxysilane, of formula:

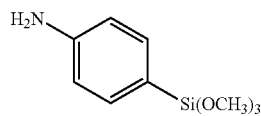

N-(2-aminoethylaminomethyl)phenethyltrirnethoxysilane, of formula:

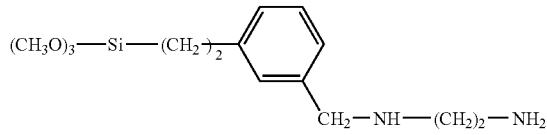

The at least one organosilicon compound may be present in the ready-to-use cosmetic composition and in the pretreatment composition in amounts ranging from 0.1% to 40% by weight, for example from 0.2% to 20% by weight and for example from 0.5% to 20% by weight, relative to the total weight of the composition.

The at least one organosilicon compound may be partially neutralized via a neutralizer or pH regulator, such that the neutralization reaches $1/1000$ to $99/100$ and for example from $0.2/100$ to $70/100$. For instance, in at least one embodiment, the neutralization is from $0.2/100$ to $60/100$.

The pH regulator may be at least one cosmetically acceptable acid that is soluble in the medium of the composition. Among the acids that may be used, mention may be made of hydrochloric acid, phosphoric acid, sulfonic acid, and organic acids. The composition used according to the disclosure may also comprise at least one other organic acid.

The at least one organic acid may be, for example, chosen from acids comprising at least one carboxylic, sulfonic, phosphonic, or phosphoric acid functions. They may comprise other chemical functions, for example hydroxyl or amino functions. They may be saturated or unsaturated. Mention may be made for example of acetic acid, propanoic acid, butanoic acid, lactic acid, glycolic acid, ascorbic acid, maleic acid, phthalic acid, succinic acid, taurine, tartaric acid, gluconic acid, glucuronic acid, and citric acid. For instance, in at least one embodiment, the at least one organic acid can be chosen from lactic acid, acetic acid and citric acid.

This partial neutralization of the sparingly polymerized or unpolymerized at least one organosilicon compound of the compositions of the disclosure is related to obtaining the desired properties for the compositions.

For the purposes of the present disclosure, the term "polymer" means a compound corresponding to the repetition of at least one unit (the unit being derived from compounds known as monomers). This at least one unit is repeated at least twice and for example at least three times.

The term "hydrophobic polymer" means a polymer that has a solubility in water at 25° C. of less than 1% by weight.

The term "film-forming" polymer means a polymer that is capable, by itself or in the presence of an auxiliary film-forming agent, of forming a macroscopically continuous film on a support, for example on keratin materials, and for instance a cohesive film.

In at least one embodiment, the at least one hydrophobic film-forming organic polymer is at least one polymer chosen from the group comprising:

film-forming polymers that are soluble in an organic solvent medium, such as liposoluble polymers. This means that the polymer is soluble or miscible in the organic medium and forms a single homogeneous phase when it is incorporated into the medium;

film-forming polymers that are dispersible in an organic solvent medium, which means that the polymer forms an insoluble phase in the organic medium, the polymer remaining stable and/or compatible once incorporated into this medium. For example, such polymers may be in the form of non-aqueous dispersions of polymer particles, such as dispersions in silicone oils or hydrocarbon-based oils. In at least one embodiment, the non-aqueous polymer dispersions comprise polymer particles stabilized on their surface with at least one stabilizer. These non-aqueous dispersions may be referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles may be referred to as latices. In this case, the composition must comprise an aqueous phase.

Among the at least one hydrophobic film-forming polymer that may be used in the composition of the present disclosure, mention may be made of synthetic polymers, of radical type or of polycondensate type, polymers of natural origin, and mixtures thereof. Hydrophobic film-forming polymers that may be mentioned for example include acrylic polymers, polyurethanes, polyesters, polyamides, polyureas, cellulose-based polymers such as nitrocellulose, silicone polymers, polyamide polymers and copolymers, and polyisoprenes.

The at least one hydrophobic film-forming polymer may be chosen from the film-forming polymers described in patent application WO 04/028 487.

The at least one hydrophobic film-forming polymer may for example be chosen from:

a) Homopolymers and copolymers of olefins; cycloolefins; butadiene; isoprene; styrene; vinyl ethers, esters or amides; (meth)acrylic acid esters or amides containing a linear, branched or cyclic C1-C20 alkyl group, a C6-C10 aryl group or a C2-C6 hydroxyalkyl group.

Such homopolymers and copolymers may be obtained from monomers chosen from the group constituted by isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, ethyl (meth)acrylate, methyl (meth)acrylate, tert-butyl (meth)acrylate, tridecyl (meth)acrylate, stearyl (meth)acrylate, hydroxyethyl (meth)acrylate, 2-hydroxypropyl (meth)acrylate, benzyl acrylate, and phenyl acrylate, or mixtures thereof. Amides of the acid monomers that may be mentioned include (meth) acrylamides, and for example N-alkyl (meth)acrylamides, such as of a C2-C12 alkyl, such as N-ethylacrylamide, N-t-butylacrylamide and N-octylacrylamide; N-di(C1-C4)alkyl (meth)acrylamides and perfluoroalkyl (meth)acrylates. The above polymers may also comprise as monomers small amounts of an unsaturated carboxylic or sulfonic acid such as acrylic acid, methacrylic acid or AMPS, on condition that the overall nature of the polymer remains hydrophobic.

As other vinyl monomers that may be used, mention may also be made of:

N-vinylpyrrolidone, vinylcaprolactam, vinyl N—(C1-C6) alkylpyrroles, vinyloxazoles, vinylthiazoles, vinylpyrimidines, and vinylimidazoles, olefins such as ethylene, propylene, butenes, isoprene, and butadienes.

The vinyl polymer may be crosslinked using at least one difunctional monomer, for instance comprising at least two ethylenic unsaturations, such as ethylene glycol dimethacrylate or diallyl phthalate.

Mention will be made, for example, of the alkyl acrylate/ cycloalkyl acrylate copolymer sold by Phoenix Chem. under the name GIOVAREZ AC-5099 ML, the acrylates/C12-22 alkyl methacrylate copolymer sold by Rohm & Haas under the name SOLTEX OPT and vinylpyrrolidone copolymers, such as copolymers of a C2-C30 alkene, such as a C3-C22 alkene, and combinations thereof. As examples of VP copolymers that may be used in the disclosure, mention may also be made of the VP/vinyl laurate copolymer, the VP/vinyl stearate copolymer, the butylated polyvinylpyrrolidone (PVP) copolymer, the VP/hexadecene copolymer sold by ISP under the name GANEX V216, the VP/eicosene copolymer sold by ISP under the name GANEX V220, the VP/triacontene copolymer or the VP/acrylic acid/lauryl methacrylate copolymer. Mention may also be made of the copolymers whose CTFA name (4th edition, 1991) is octylacrylamide/acrylates/butylaminoethyl methacrylate copolymer, such as the products sold under the name AMPHOMER® or LOVOCRYL® 47 by the company National Starch, and also the copolymers whose CTFA name is acrylates/octylacrylamide copolymer, such as the products sold under the name DERMACRYL® LT or DERMACRYL® 79 by the company National Starch.

For example, polymers that may be mentioned include:

i) polymers bearing fluoro groups belonging to one of the classes described in the above text, for example the Fomblin products described in patent U.S. Pat. No. 5,948,393, and the copolymers of alkyl (meth)acrylate/ perfluoroalkyl (meth)acrylate described in patents EP 0 815 836 and U.S. Pat. No. 5,849,318.

ii) polymers or copolymers resulting from the polymerization or copolymerization of an ethylenic monomer, comprising at least one ethylenic bond, which can be for example conjugated (or dienes). As polymers or copolymers resulting from the polymerization or copolymerization of an ethylenic monomer, vinyl, acrylic, or methacrylic copolymers can be used.

In at least one embodiment, the at least one hydrophobic film-forming polymer is a block copolymer comprising at least one block constituted of styrene units or styrene derivatives (for example methylstyrene, chlorostyrene, or chloromethylstyrene). The copolymer comprising at least one styrene block may be a diblock or triblock copolymer, or even a multiblock, star or radial copolymer. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block or a methacrylate (MA) block, or a combination of these blocks. The copolymer comprising at least one block constituted of styrene units or styrene derivatives may be a diblock or triblock copolymer, and for example of the polystyrene/polyisoprene or polystyrene/polybutadiene type, such as those sold or manufactured under the name LUVITOL HSB by BASF and those of the polystyrene/copoly(ethylene-propylene) type or alternatively of the polystyrene/copoly(ethylene/butylene) type, such as those sold or manufactured under the brand name KRATON by Shell Chemical Co. or GELLED PERMETHYL 99A by Penreco.

Non-limiting mention may be made, for example, of KRATON G1650 (SEBS), KRATON G1651 (SEBS), KRATON G1652 (SEBS), KRATON G1657X (SEBS), KRATON G1701X (SEP), KRATON G1702X (SEP), KRATON G1726X (SEB), KRATON D-1101 (SBS), KRATON D-1102 (SBS), KRATON D-1107 (SIS), GELLED PERMETHYL 99A-750, GELLED PERMETHYL 99A-753-58 (mixture of star block polymer and of triblock polymer), GELLED PERMETHYL 99A-753-59 (mixture of star block polymer and of triblock polymer), VERSAGEL MD 970 and VERSAGEL MD 960 from Penreco (mixture of star polymer and of triblock polymer in isododecane).

Styrene-methacrylate copolymers may also be used, such as the polymers sold under the references OS129880, OS129881 and OS 84383 from Lubrizol (styrene-methacrylate copolymer).

In at least one embodiment, the at least one hydrophobic film-forming polymer is chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer which is chosen from vinyl esters (other than the vinyl ester already present), α-olefins (containing from 8 to 28 carbon atoms), alkyl vinyl ethers (in which the alkyl group contains from 2 to 18 carbon atoms) or allylic or methallylic esters (containing a linear or branched saturated hydrocarbon-based radical of 1 to 19 carbon atoms, bonded to the carbonyl of the ester group).

These copolymers may be partially crosslinked using crosslinking agents that may be either of the vinyl type or of the allylic or methallylic type, such as tetraallyloxyethane, divinylbenzene, divinyl octanedlioate, divinyl dodecanedioate, and divinyl octadecanedioate.

Non-limiting examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate crosslinked with 0.2% divinylbenzene.

iii) Polyalkenes and copolymers of C2-C20 alkenes, such as polybutene.

iv) Polymers of natural origin, which are optionally modified, which may be chosen from shellac resin, sandarac gum, dammar resins, elemi gums and copal resins, polysaccharides comprising alkyl (ether or ester) side chains for example alkylcelluloses containing a linear or branched, saturated or unsaturated C1-C8 alkyl radical, such as ethylcellulose and propylcellulose.

The at least one hydrophobic film-forming polymer of natural origin may be chosen for example from cellulose-based polymers such as nitrocellulose, cellulose acetate, cellulose acetobutyrate, or cellulose aceto propionate. Examples that may be mentioned include the ethylcellulose sold by Aqualon under the reference AQUALON ETHYLCELLULOSE N200, the cellulose acetobutyrate sold by Eastman Chemical under the reference CAB-381-0.5, and the cellulose acetopropionates sold by Eastman Chemical under the references CAP-482-20 and CAP-504-0.2.

v) Polycondensates.

Among the polycondensates that may be mentioned are nonionic polyurethanes, polyurethane-acrylics, polyurethane-polyvinylpyrrolidones, polyester-polyurethanes, polyether-polyurethanes, polyureas and polyurea-polyurethanes, and mixtures thereof.

The polyurethanes may be, for example, a copolymer of aliphatic, cycloaliphatic or aromatic polyurethane or of polyurea-polyurethane.

The polyurethanes as defined in the present disclosure may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting mention may also be made of polyesters, polyester amides, fatty-chain polyesters, polyamides, and epoxyester resins.

The polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol and 4,4-N-(1-methylpropylidene)bisphenol may be used as aliphatic diols.

The polyesteramides may be obtained in a manner similar to that for the polyesters, via the polycondensation of diacids with amino alcohols. The polyamides may be obtained in a manner similar to that for the polyesters, via the polycondensation of diacids with diamines.

For example polyesters that may be mentioned include aliphatic polyesters comprising C4-50 alkyl side chains or polyesters resulting from the condensation of fatty acid dimers, or alternatively polyesters comprising a silicone segment in the form of a terminal block, graft or group, as defined in patent application FR 0 113 920.

b) Silicone compounds.

The at least one hydrophobic film-forming polymer may also be a polymer comprising at least one silicone portion.

In the present disclosure, the terms "silicone" and "polysiloxane" mean any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond =Si—O—Si=), optionally substituted hydrocarbon-based radicals being bonded directly via a carbon atom to the said silicon atoms. The most common hydrocarbon-based radicals are alkyl radicals, for instance of $C_1$-$C_{10}$ and for example methyl, fluoroalkyl radicals, aryl radicals and for instance phenyl, and alkenyl radicals and for example vinyl. Other types of radicals that may be bonded, either directly or via a hydrocarbon-based radical, to the siloxane chain are for example hydrogen, halogens and for instance chlorine, bromine or fluorine, thiols, alkoxy radicals, polyoxyalkylene (or polyether) radicals and for example polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulfosuccinates, thiosulfates, phosphates and sulfates. This list is not intended to be limiting ("organomodified" silicones).

As the at least one hydrophobic film-forming polymer comprising at least one silicone portion, non-limiting mention may be made for example of:

i) silicone resins, which are generally soluble or swellable in silicone oils.

These resins are crosslinked polymers of polyorganosiloxanes.

The nomenclature of silicone resins is known under the name MDTQ, the resin being described as a function of the various siloxane monomer units it comprises, each of the letters MDTQ characterizing a type of unit.

The letter M represents the monofunctional unit of formula $(CH_3)_3SiO_{1/2}$, the silicon atom being connected to only one oxygen atom in the polymer comprising this unit.

The letter D means a difunctional unit $(CH_3)_2SiO_{2/2}$ in which the silicon atom is connected to two oxygen atoms.

The letter T represents a trifunctional unit of formula $(CH_3)SiO_{3/2}$.

In the units M, D and T defined previously, at least one of the methyl groups may be substituted with a group R other than a methyl group, such as a hydrocarbon-based radical (for example alkyl) containing from 2 to 10 carbon atoms or a phenyl group, or alternatively a hydroxyl group.

Finally, the letter Q means a tetrafunctional unit $SiO_{4/2}$ in which the silicon atom is bonded to four hydrogen atoms, which are themselves bonded to the rest of the polymer.

Various resins with different properties may be obtained from these different units, the properties of these polymers varying as a function of the type of monomers (or units), of the type and number of substituted radicals, of the length of the polymer chain, of the degree of branching and of the size of the side chains.

Examples of these silicone resins that may be mentioned include:
- siloxysilicates, which may be trimethyl siloxysilicates of formula $[(CH_3)_3.Si.O]_x.(SiO_{4/2})_y$ (units MQ) in which x and y are integers ranging from 50 to 80,
- polysilsesquioxanes of formula $(CH_3SiO_{3/2})_x$ (units T) in which x is greater than 100 and in which at least one of the methyl radicals may be substituted with a group R as defined above, and
- polymethylsilsesquioxanes, which are polysilsesquioxanes in which none of the methyl radicals is substituted with another group. Such polymethylsilsesquioxanes are described in U.S. Pat. No. 5,246,694.
- Non-limiting examples of commercially available polymethylsilsesquioxane resins that may be mentioned include those sold:
- by the company Wacker under the reference RESIN MK, such as BELSIL PMS MK: polymer comprising $CH_3SiO_{3/2}$ repeating units (units T), which may also comprise up to 1% by weight of $(CH_3)_2SiO_{2/2}$ units (units D) and having an average molecular weight of about 10,000, and
- by the company Shin-Etsu under the references KR-220L, which are compounds of units T of formula $CH_3SiO_{3/2}$ and have Si—OH (silanol) end groups, under the reference KR-242A, which comprise 98% of units T and 2% of dimethyl units D and have Si—OH end groups, or alternatively under the reference KR-251, comprising 88% of units T and 12% of dimethyl units D and have Si—OH end groups.

Siloxysilicate resins that may be mentioned in a non-limiting manner include trimethyl siloxysilicate (TMS) resins, optionally in the form of powders. Such resins are sold under the reference SR1000 by the company General Electric or under the reference TMS 803 by the company Wacker. Non-limiting mention may also be made of the trimethyl siloxysilicate resins sold in a solvent such as cyclomethicone, sold under the name KF-7312J by the company Shin-Etsu or DC 749 or DC 593 by the company Dow Corning.

ii) Silicone polyamides of the polyorganosiloxane type such as those described in documents U.S. Pat. Nos. 5,874,069, 5,919,441, 6,051,216 and 5,981,680.

iii) Grafted silicone compounds

The compositions of the disclosure may also comprise at least one grafted silicone polymer. In the context of the present disclosure, the term "grafted silicone polymer" means a polymer comprising a polysiloxane portion and a portion constituted of a non-silicone organic chain, one of the two portions constituting the main chain of the polymer, the other being grafted onto the main chain.

The at least one grafted silicone polymer used in the cosmetic composition according to the disclosure can be for example chosen from the group constituted by polymers with a non-silicone organic backbone grafted with monomers containing a polysiloxane, and polymers with a polysiloxane backbone grafted with non-silicone organic monomers.

The non-silicone organic monomers constituting the main chain of the at least one grafted silicone polymer may be chosen from radical-polymerizable ethylenically unsaturated monomers, polycondensation-polymerizable monomers such as those forming polyamides, polyesters or polyurethanes, and ring-opening monomers such as those of the oxazoline or caprolactone type.

The polymers comprising a non-silicone organic backbone grafted with monomers containing a polysiloxane, in accordance with the disclosure, may be chosen from those described in patents U.S. Pat. Nos. 4,693,935, 4,728,571 and 4,972,037 and patent applications EP-A-0 412 704, EP-A-0 412 707, EP-A-0 640 105 and WO 95/00578. They are copolymers obtained by radical polymerization starting with ethylenically unsaturated monomers and silicone macromers containing a vinyl end group, or alternatively copolymers obtained by reacting a polyolefin comprising functionalized groups with a polysiloxane macromer containing an end function that is reactive with the said functionalized groups.

The polymer containing a non-silicone organic backbone grafted with monomers containing a polysiloxane may, for example, have the following structure:

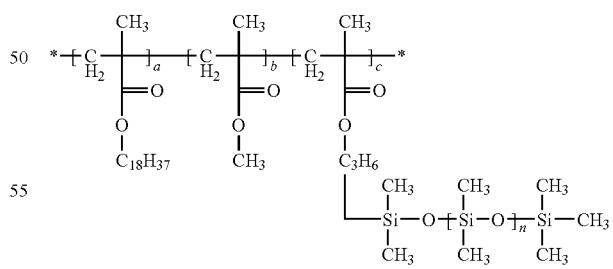

Such a polymer is sold under the name KP 561 by Shin-Etsu.

The copolymer containing a non-silicone organic backbone grafted with monomers containing a polysiloxane may also have the following structure:

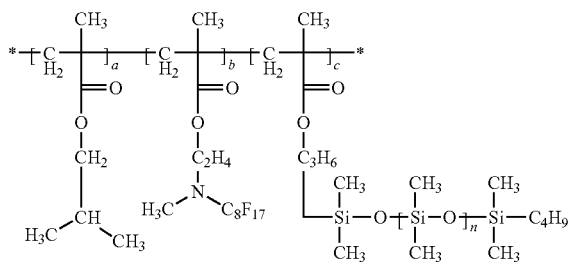

Such a polymer, Polysilicone 7, is sold under the name SA70 by 3M.

Other copolymers comprising a non-silicone organic backbone grafted with monomers containing a polysiloxane may also be KP545, KP574 and KP575 sold by Shin-Etsu.

A grafted silicone compound that may also be mentioned is the isobutyl methacrylate/bis-hydroxypropyl dimethicone acrylate copolymer sold by Grant Industries under the name GRANACRYSIL BMAS.

According to the present disclosure, the at least one grafted silicone polymer, containing a polysiloxane backbone grafted with non-silicone organic monomers, comprises a main silicone chain (or polysiloxane (≡Si—O—)$_n$) onto which is grafted, within the said chain and also optionally on at least one of its ends, at least one organic group not comprising silicone.

Examples of silicone polymers corresponding to the definition are for example polydimethylsiloxanes (PDMS) onto which are grafted, via a connecting chain unit of thiopropylene type, mixed polymer units of the poly(meth)acrylic acid type and of the polyalkyl (meth)acrylate type. A compound corresponding to this definition that may be mentioned is the poly dimethyl/methyl siloxane containing methyl 3-thiopropyl acrylate/methyl methacrylate/methacrylic acid groups or Polysilicone-8 sold under the name VS80 by the company 3M.

Other examples of silicone polymers are for example polydimethylsiloxanes (PDMS) onto which are grafted, via a connecting chain unit of thiopropylene type, polymer units of the polyisobutyl (meth)acrylate type.

For example, the number-average molecular mass of the silicone polymers containing a polysiloxane backbone grafted with non-silicone organic monomers of the disclosure may range from 10,000 to 1,000,000 and for instance from 10,000 to 100,000.

For example, the at least one grafted silicone polymer may be chosen from the group constituted by the copolymer of polydimethylsiloxane-grafted alkyl methacrylate, copolymers of isobutyl methacrylate, of acrylic acid and of silicone macromer, and the poly dimethyl/methyl siloxane comprising methyl 3-thiopropyl acrylate/methyl methacrylate/methacrylic acid groups.

iv) Polyurea/urethane Silicones

The copolymer of the disclosure may comprise, in addition to the polysiloxane/polyurea, other blocks of different units. Non-limiting mention can be made for example of polysiloxane/polyurea/polyurethane block terpolymers.

According to at least one embodiment, the copolymer contains solely at least one siloxane block and at least one polyurea block.

According to the disclosure, the copolymer may correspond to the general formula (IV):

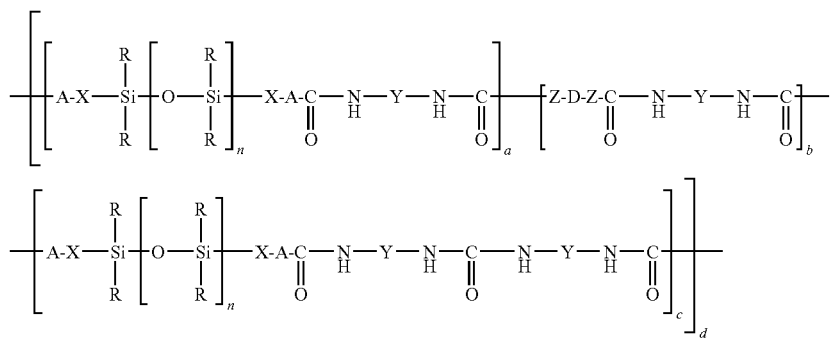

wherein:
R represents a monovalent hydrocarbon-based radical, where appropriate substituted with fluorine or chlorine, containing 1 to 20 carbon atoms,
X represents an alkylene radical containing 1 to 20 carbon atoms, wherein non-neighboring methylene units may be replaced with —O— radicals,
A represents an oxygen atom or an amino radical —NR'—,
Z represents an oxygen atom or an amino radical —NR'—,
R' represents hydrogen or an alkyl radical containing 1 to 10 carbon atoms,
Y represents a divalent hydrocarbon-based radical, where appropriate substituted with fluorine or chlorine, containing 1 to 20 carbon atoms,
D represents an alkylene radical, where appropriate substituted with fluorine, chlorine, C1-C6 alkyl or C1-C6 alkyl ester, containing from 1 to 700 carbon atoms, wherein non-neighboring methylene units may be replaced with radicals —O—, —COO—, —OCO— or —OCOO—,
n is a number ranging from 1 to 4000,
a is a number at least equal to 1,
b is a number ranging from 0 to 40,
c is a number ranging from 0 to 30, and
d is a number greater than zero,
on condition that A represents in at least one of the units (a) an NH radical.

For example, R can be a monovalent hydrocarbon-based radical of 1 to 6 carbon atoms, for example methyl, ethyl, vinyl and phenyl. According to at least one embodiment, R is an unsubstituted alkyl radical.

For example, X can be an alkylene radical containing 2 to 10 carbon atoms. For instance, in at least one embodiment, the alkylene radical X is not interrupted.

According to at least one embodiment, the group A in all the units (b) and (c), when they are present, represents NH.

According to another embodiment, all the groups A represent an NH radical.

For example, Z can be an oxygen atom or an NH radical.

For example, Y can be a hydrocarbon-based radical containing from 3 to 13 carbon atoms, which is for instance unsubstituted. For example, Y can be a linear or cyclic aralkylene or alkylene radical.

For example, D can be an alkylene radical containing at least two and for example at least four carbon atoms, and not more than 12 carbon atoms.

For example, D can be a polyoxyalkylene radical, such as a polyoxyethylene or polyoxypropylene radical containing at least 20 and for example at least 100 carbon atoms, and not more than 800 and for example not more than 200 carbon atoms.

For instance, in at least one embodiment, the radical D is unsubstituted.

For instance, n can be a number equal to at least 3 and for example at least 25, and for example not more than 800, such as not more than 400 and for instance not more than 250.

For example, a can be a number greater than 50.

When b is other than 0, b for example can be a number not greater than 50 and for instance not greater than 25.

For example, c can be a number not greater than 10 and for instance not greater than 5.

The copolymers of the disclosure may be obtained according to the polymerization processes described in patent application publication number US 2004/0254325 or patent application WO 03/014 194.

According to at least one embodiment, the copolymer is a nonionic polysiloxane/polyurea copolymer, i.e. it does not comprise any ionized or ionizable groups.

An example of a copolymer that may be mentioned is the dimethylpolysiloxane/urea copolymer, of INCI name polyurea dimethicone.

Such a polymer may be obtained for instance by copolymerization of an α,ω-aminosilicone with a diisocyanate. Polymers corresponding to these characteristics are, for example, the products sold under the references WACKER-BELSIL® UD 60, WACKER-BELSIL® UD 80, WACKER-BELSIL® UD 140 and WACKER-BELSIL® UD 200 by the company Wacker.

v) Copolymers Based on Silicone Resin and on Fluid Silicone

These silicone copolymers are obtained by reacting a silicone resin and a fluid silicone.

Such copolymers are described, for example, in *Silicone Pressure Sensitive Adhesive*, Sobieski and Tangney, Handbook of Pressure Sensitive Adhesive Technology (D. Satas Ed.), von Nostrand Reinhold, New York.

In the copolymer, the silicone resin is present in an amount ranging from 45% to 75% (relative to the total mass of silicone) and the fluid silicone is present in an amount ranging from 25% to 55%, with the sum of the percentages of silicone resin and of fluid silicone being equal to 100. For example, the silicone resin can be present in an amount ranging from 55% to 65% (relative to the total mass of silicone) and the fluid silicone can be present in an amount ranging from 35% to 45%, with the sum of the percentages of silicone resin and of fluid silicone being equal to 100.

For example, the silicone resin according to the disclosure may be the product of condensation of $SiO_2$ groups and of $R3(SiO)_{1/2}$ (triorganosilyl) groups for which each group R is independently selected from methyl, ethyl, propyl and vinyl radicals and for which the ratio between the $SiO_2$ functions and the $R3(SiO)_{1/2}$ functions of the silicone resin ranges from 0.6 to 0.9. Triorganosilyl groups that may be used to form the silicone resin may be trimethylsilyl, triethylsilyl, methylmethylpropylsilyl and dimethylvinylsilyl units, and mixtures thereof. The trimethylsilyl group is an example in the context of the disclosure.

For example, the fluid silicone according to the disclosure can be a diorganopolysiloxane containing OH end functions, having a viscosity ranging from 100 to 100,000 cSt at 25° C., for which the substituents of the diorganopolysiloxane are chosen independently from methyl, ethyl, propyl, and vinyl radicals. The diorganosiloxanes can be for instance linear polymers. Examples of diorganopolysiloxanes may be, in a non-limiting manner, a polydimethylsiloxane, an ethylmethylpolysiloxane, the copolymer of dimethylsiloxane and of methylvinylsiloxane, and mixtures of such polymers or copolymers containing OH end groups. An example of a diorganopolysiloxane is a polydimethylsiloxane.

Examples of synthesis of such a copolymer are described, for example, in patent U.S. Pat. No. 5,162,410 or in patent CA 711 756.

Examples of copolymers according to the disclosure are sold by Dow Corning under the reference BIO-PSA®, these BIO-PSA® copolymers themselves possibly being in two forms, standard or amine-compatible, and being supplied in different solvents with several silicone resin/fluid silicone ratios. Mention may be made for example of the grades 7-4400, 7-4500 and 7-4600. For instance, a BIO-PSA® that can be used according to the disclosure is the grade 7-4400.

When the film-forming polymer according to the disclosure is dispersed in the organic solvent, the compositions according to the disclosure may comprise at least one stable dispersion of essentially spherical polymer particles of at least one polymer. Before incorporating them into the composition of the disclosure, the particles are generally dispersed in a physiologically acceptable liquid fatty phase, such as hydrocarbon-based oils or silicone oils. According to at least one embodiment, these dispersions are generally known as "NAD"s (non-aqueous dispersions) of polymer, as opposed to networks, which are aqueous dispersions of polymer.

These dispersions may for example be in the form of polymer nanoparticles stably dispersed in the said liquid organic phase. The nanoparticles for example may have a mean size ranging from 5 to 800 nm, such as from 50 to 500 nm. However, it is possible to obtain polymer particle sizes ranging up to 1 μm.

The polymers in dispersion that may be used in the compositions of the disclosure for example have a molecular weight ranging from about 2,000 to 10,000,000 and a Tg ranging from −100° C. to 300° C., such as from −10° C. to 80° C.

Among the film-forming polymers in dispersion, mention may be made of acrylic or vinyl radical homopolymers or copolymers, such as with a Tg of less than or equal to 40° C. and for example ranging from −10° C. to 30° C., used alone or as a mixture.

According to at least one embodiment, the polymer particles are stabilized with a stabilizer that is solid at room temperature, which may be a block polymer, a grafted polymer and/or a statistical polymer, alone or as a mixture. The stabilization may be achieved by any known method, and for example by direct addition of the stabilizing polymer during the polymerization.

When an aqueous dispersion of polymer particles is used, the solids content of the aqueous dispersion may be of the order of 3% to 60% and for instance from 10% to 50% by weight.

The size of the polymer particles in aqueous dispersion may range from 10 to 500 nm and may range for example from 20 to 150 nm, allowing the production of a film that has appreciable gloss. However, particle sizes ranging up to one micron may be used.

In a non-limiting manner, the at least one hydrophobic film-forming polymer can be chosen from polyurethanes; polyurethane-acrylics; polyureas; polyurea-polyurethanes; polyester-polyurethanes; polyether-polyurethanes; polyesters; polyester amides; acrylic polyesters; acrylic and/or vinyl polymers or copolymers; polyacrylamides; acrylic polyesters; polyvinylpyrrolidone-based polymers or copolymers; silicone polymers; silicone polymers comprising polyurethane, polyurea or acrylic parts; silicone resins; copolymers based on silicone resin and dimethiconol; fluoro polymers; celluloses, and mixtures thereof. According to at least one embodiment, the at least one hydrophobic film-forming polymer is chosen from acrylic polymers or copolymers, acrylic polyesters, polyvinylpyrrolidone-based polymers or copolymers, silicone resins, copolymers based on silicone resin and dimethiconol, silicone polymers comprising polyurethane, polyurea or acrylic parts; and celluloses.

The at least one hydrophobic film-forming polymer according to the disclosure may be selected on the basis of its mechanical properties. Such properties may be the flexibility, the hardness, the adhesion, the remanence, the resistance to water or to other chemical compounds, and the abrasion resistance. It is also possible to take advantage of the more versatile properties of block polymers (polymers constituted of two or more distinct polymer segments), grafted polymers (polymers containing a polymeric side chain grafted onto the homopolymer or copolymer backbone) or heteropolymers (polymers comprising two or more different monomers). In the copolymers, for example, the amount of hard and soft blocks may have an impact on the properties of the polymer.

Furthermore, it is possible to mix at least two polymers in order to achieve the desired property. Examples of combinations may be polyurethane and polyacrylates, polyurethane and polyesters, two polymers having a silicone portion, or polyurethane and a polymer having a silicone portion.

According to at least one embodiment, the at least one hydrophobic film-forming polymer is a nonionic polymer. According to another embodiment, the at least one hydrophobic film-forming polymer is solid at 25° C., in the sense that no flowing is observed with the naked eye after one hour.

The at least one hydrophobic film-forming polymer may be present in the compositions according to the disclosure in an amount ranging from 0.1% to 40% by weight, for example ranging from 0.1% to 30% by weight, such as ranging from 0.5% to 20% by weight, such as ranging from 1% to 20% by weight and for instance ranging from 1% to 15% by weight, relative to the total weight of the composition.

When the glass transition temperature of the polymer is too high for the desired use, at least one plasticizer may be combined therewith so as to lower this temperature of the mixture used. The at least one plasticizer may be chosen from the plasticizers usually used in the field of application, and for example from compounds that may be solvents for the polymer.

For instance, the at least one plasticizer can have a molecular mass of less than or equal to 5,000 g/mol, such as less than or equal to 2,000 g/mol, such as less than or equal to 1,000 g/mol and for instance less than or equal to 900 g/mol. The at least one plasticizer may have for example a molecular mass of greater than or equal to 100 g/mol.

Thus, the cosmetic compositions according to the disclosure may also comprise at least one plasticizer. For example, mention may be made, alone or as a mixture, of common plasticizers such as:

glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;

polyethylene glycols, polypropylene glycols, polyethylene glycol-polypropylene glycol copolymers, and mixtures thereof, for example high molecular weight polypropylene glycols, for example having a molecular mass ranging from 500 to 15,000, for instance glycol esters;

propylene glycol derivatives and for example propylene glycol phenyl ether, propylene glycol diacetate, dipropylene glycol ethyl ether, tripropylene glycol methyl ether and diethylene glycol methyl ether, dipropylene glycol butyl ether. Such compounds are sold by Dow Chemical under the names DOWANOL PPH and DOWANOL DPNB;

acid esters, for example of carboxylic acids, such as citrates, phthalates, adipates, carbonates, tartrates, phosphates and sebacates;

esters derived from the reaction of a monocarboxylic acid of formula $R_{11}COOH$ with a diol of formula $HOR_{12}OH$ in which $R_{11}$ and $R_{12}$, which may be identical or different, represent a linear, branched or cyclic, saturated or unsaturated hydrocarbon-based chain for example comprising from 3 to 15 carbon atoms, optionally comprising at least one heteroatom such as N, O or S, for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical;

oxyethylenated derivatives, such as oxyethylenated oils, for example plant oils, such as castor oil; and mixtures thereof.

For instance, the at least one plasticizer may be chosen from esters of at least one carboxylic acid comprising 1 to 7 carbon atoms and of a polyol comprising at least 4 hydroxyl groups.

The polyol according to the disclosure may be a cyclized or uncyclized saccharide—polyhydroxyaldehyde (aldose) or polyhydroxyketone (ketose). The polyol can be for example a saccharide cyclized in hemiacetal form.

The polyol may be a monosaccharide or a polysaccharide comprising from 1 to 10 saccharides, such as from 1 to 4 saccharides and such as one or two saccharides. The polyol may be chosen from erythritol, xylitol, sorbitol, glucose, sucrose, lactose and maltose.

The polyol according to the disclosure can be for example a disaccharide. Among the disaccharides, non-limiting mention may be made of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and for example sucrose.

The ester according to the disclosure may be constituted of a polyol esterified with at least two different monocarboxylic acids, or with at least three different monocarboxylic acids.

The ester according to the disclosure may be a copolymer of two esters, for example a copolymer i) of a sucrose substituted with benzoyl groups and ii) of a sucrose substituted with acetyl and/or isobutyryl groups.

The carboxylic acid can be for instance a monocarboxylic acid comprising from 1 to 7 carbon atoms and for instance from 1 to 5 carbon atoms, chosen, for example, from acetic acid, n-propanoic acid, isopropanoic acid, n-butanoic acid, isobutanoic acid, tert-butanoic acid, n-pentanoic acid and benzoic acid.

The ester may be obtained from at least two different monocarboxylic acids. According to at least one embodiment, the acid is an unsubstituted linear or branched acid.

The acid can be for instance chosen from acetic acid, isobutyric acid and benzoic acid, and mixtures thereof.

According to at least one embodiment, the ester is sucrose diacetate hexakis(2-methylpropanoate), such as the product sold under the name SUSTANE SAIB FOOD GRADE KOSHER by the company Eastman Chemical.

According to another embodiment, the at least one plasticizer may be chosen from esters of an aliphatic or aromatic polycarboxylic acid and of an aliphatic or aromatic alcohol containing from 1 to 10 carbon atoms.

The aliphatic or aromatic alcohol can comprise from 1 to 10 and for example from 1 to 8 carbon atoms, for example from 1 to 6 carbon atoms. It may be chosen from alcohols R1OH such that R1 represents methyl, ethyl, propyl, isopropyl, butyl, hexyl, ethylhexyl, decyl, isodecyl, benzyl, or benzyl substituted with an alkyl containing 1 to 3 carbon atoms, and mixtures thereof.

The aliphatic or aromatic polycarboxylic acid for example may contain from 3 to 12 carbon atoms, such as from 3 to 10 carbon atoms and for instance from 3 to 8 carbon atoms, for example 6 or 8 carbon atoms.

The aliphatic or aromatic polycarboxylic acid may be chosen, for example, from dicarboxylic acids and tricarboxylic acids.

Among the aliphatic dicarboxylic acids that may be mentioned are those of formula $HOOC-(CH_2)_n-COOH$, in which n is an integer ranging from 1 to 10 and for instance ranging from 2 to 8, for example equal to 2, 4, 6, or 8.

The dicarboxylic acids may be chosen from succinic acid, adipic acid and sebacic acid.

Among the aromatic dicarboxylic acids, mention may be made of phthalic acid.

Among the tricarboxylic acids, mention may be made of the triacids that correspond to formula

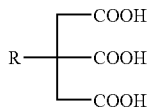

in which R represents a group —H, —OH or —OCOR' in which R' represents an alkyl group containing from 1 to 6 carbon atoms. For example, R can represent a group —OCOCH$_3$.

The tricarboxylic acid for example may be chosen from acetylcitric acid, butyroylcitric acid and citric acid.

Among the tricarboxylic acid esters that may be used are esters derived from citric acid (or citrates) such as tributyl acetyl citrate, triethyl acetyl citrate, triethylhexyl acetyl citrate, trihexyl acetyl citrate, trihexyl butyroyl citrate, triisodecyl citrate, triisopropyl citrate, tributyl citrate and tris(2-ethylhexyl) citrate. As commercial references of plasticizers mentioned above, mention may be made of the Citroflex range sold by Vertellus, such as, CITROFLEX A4 and CITROFLEX C2.

Among the adipic acid esters that may be mentioned are dibutyl adipate and bis(2-ethylhexyl) adipate.

Among the sebacic acid esters that may be mentioned are dibutyl sebacate, bis(2-ethylhexyl) sebacate, diethyl sebacate and diisopropyl sebacate.

Among the succinic acid esters that may be mentioned are bis(2-ethylhexyl) succinate and diethyl succinate.

Among the phthalic acid esters that may be mentioned are butyl benzyl phthalate, dibutyl phthalate, diethylhexyl phthalate, diethyl phthalate and dimethyl phthalate.

For example, the at least one plasticizer may be present in the composition in an amount such that the mass ratio value between the at least one hydrophobic film-forming polymer and the at least one plasticizer ranges from 0.5 to 100, such as from 1 to 50 and for example from 1 to 10.

The ready-to-use cosmetic composition and the cosmetic composition comprising the at least one hydrophobic film-forming polymer according to the disclosure comprises at least one pigment.

The term "pigment" means any pigment that gives keratin materials color. Their stability in water at 25° C. and at atmospheric pressure (760 mmHg) is less than 0.05% and for example less than 0.01%.

The at least one pigment that may be used can be for example chosen from the organic and/or mineral pigments known in the art, such as those described in Kirk-Othmer's Encyclopaedia of Chemical Technology and in Ullmann's Encyclopaedia of Industrial Chemistry.

The at least one pigment may be in the form of powder or of pigmentary paste. It may be coated or uncoated.

The at least one pigment may be chosen, for example, from mineral pigments, organic pigments, lakes, pigments with special effects such as nacres or glitter flakes.

The at least one pigment may be a mineral pigment. The term "mineral pigment" means any pigment that satisfies the definition in Ullmann's encyclopaedia in the chapter on inorganic pigments. Among the mineral pigments that are useful in the present disclosure, non-limiting mention may be made of iron oxides, chromium oxides, manganese violet, ultramarine blue, chromium hydrate, ferric blue, and titanium oxide.

The at least one pigment may be an organic pigment. The term "organic pigment" means any pigment that satisfies the definition in Ullmann's encyclopaedia in the chapter on organic pigments. The at least one organic pigment may be chosen for example from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane, and quinophthalone compounds.

For example, the at least one white or colored organic pigment may be chosen from carmine, carbon black, aniline black, melanin, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The at least one pigment in accordance with the disclosure may also be in the form of composite pigments as described in patent EP 1 184 426. These composite pigments may be compounds for example of particles comprising a mineral core, at least one binder for ensuring the binding of the organic pigments to the core, and at least one organic pigment at least partially covering the core.

The organic pigment may also be a lake. The term "lake" means dyes adsorbed onto insoluble particles, the assembly thus obtained remaining insoluble during use.

The inorganic substrates onto which the dyes are adsorbed can be, for example, alumina, silica, calcium sodium borosilicate, or calcium aluminium borosilicate, and aluminium.

Among the dyes, mention may be made of cochineal carmine. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The at least one pigment may also be a pigment with special effects. The term "pigments with special effects" means pigments that generally create a non-uniform colored appearance (characterized by a certain shade, a certain vivacity and a certain lightness) that changes as a function of the conditions of observation (light, temperature, observation angles, etc.). They thus contrast with white or colored pigments that afford a standard uniform opaque, semi-transparent or transparent shade.

Several types of pigment with special effects exist: those with a low refractive index, such as fluorescent, photochromic or thermochromic pigments, and those with a high refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye for example of the abovementioned type, and also nacreous pigments based on bismuth oxychloride. They may also be mica particles at the surface of which are superposed at least two successive layers of metal oxides and/or of organic dyestuffs.

The nacres may for example have a yellow, pink, red, bronze, orange, brown, gold, and/or coppery color or tint.

As illustrations of nacres that may be used in the context of the present disclosure, non-limiting mention may be made for example of the gold-colored nacres sold for instance by the company Engelhard under the name GOLD 222C (CLOISONNE), SPARKLE GOLD (TIMICA), GOLD 4504 (CHROMALITE) and MONARCH GOLD 233X (CLOISONNE); the bronze nacres sold for example by the company Merck under the name BRONZE FINE (17384) (COLORONA) and BRONZE (17353) (COLORONA) and by the company Engelhard under the name SUPER BRONZE (CLOISONNE); the orange nacres sold for example by the company Engelhard under the name ORANGE 363C (CLOISONNE) and ORANGE MCR 101 (COSMICA) and by the company Merck under the name PASSION ORANGE (COLORONA) and MATTE ORANGE (17449) (MICRONA); the brown nacres sold for example by the company Engelhard under the name NU-ANTIQUE COPPER 340XB (CLOISONNE) and BROWN CL4509 (CHROMALITE); the nacres with a copper tint sold for example by the company Engelhard under the name COPPER 340A (TIMICA); the nacres with a red tint sold for example by the company Merck under the name SIENNA FINE (17386) (COLORONA); the nacres with a yellow tint sold for example by the company Engelhard under the name YELLOW (4502) (CHROMALITE); the red nacres with a gold tint sold for example by the company Engelhard under the name SUNSTONE G012 (GEMTONE); the pink nacres sold for example by the company Engelhard under the name TAN OPALE G005 (GEMTONE); the black nacres with a gold tint sold for instance by the company Engelhard under the name NU ANTIQUE BRONZE 240 AB (TIMICA), the blue nacres sold for example by the company Merck under the name MATTE BLUE (17433) (MICRONA), DARK BLUE (117324) (COLORONA), the white nacres with a silvery tint sold for example by the company Merck under the name XIRONA SILVER, and the golden-green pink-orange nacres sold for example by the company Merck under the name INDIAN SUMMER (XIRONA), and mixtures thereof.

In addition to nacres on a mica support, multilayer pigments based on synthetic substrates such as alumina, silica, sodium calcium borosilicate or calcium aluminium borosilicate, and aluminium, may be envisaged.

Non-limiting mention may also be made of pigments with an interference effect that are not fixed onto a substrate, for instance liquid crystals (HELICONES HC from Wacker), holographic interference flakes (GEOMETRIC PIGMENTS or SPECTRA FIX from Spectratek). Pigments with special effects may also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present disclosure makes it possible to obtain a wide range of colors, and also for example optical effects such as metallic effects or interference effects.

The size of the at least one pigment used in the cosmetic composition comprising the at least one hydrophobic film-forming polymer can range, for example, from 10 nm to 200 µm, such as from 20 nm to 80 µm and for example from 30 nm to 50 µm.

The at least one pigment may be dispersed in the product via at least one dispersant.

The at least one dispersant serves to protect the dispersed particles against agglomeration or flocculation. This at least one dispersant may be a surfactant, an oligomer, a polymer or a mixture of several thereof, bearing at least one functionality with strong affinity for the surface of the particles to be dispersed. For example, it can physically or chemically attach to the surface of the at least one pigment. The at least one dispersant may also comprise at least one functional group that is compatible with or soluble in the continuous medium. For example, 12-hydroxystearic acid esters and C8 to C20 fatty acid esters of polyols such as glycerol or diglycerol can be used, such as poly(12-hydroxystearic acid) stearate with a molecular weight of about 750 g/mol, such as the product sold under the name SOLSPERSE 21000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof.

As other dispersants that may be used in the compositions of the disclosure, non-limiting mention may be made of quaternary ammonium derivatives of polycondensed fatty acids, for instance SOLSPERSE 17000 sold by the company Avecia, and polydimethylsiloxane/oxypropylene mixtures such as those sold by the company Dow Corning under the references DC2-5185 and DC2-5225 C.

The at least one pigment used in the compositions comprising the at least one hydrophobic film-forming polymer may be surface-treated with an organic agent.

Thus, the at least one pigment that has been surface-treated beforehand, which is useful in the context of the disclosure, can be a pigment that has totally or partially undergone a surface treatment of chemical, electronic, electrochemical, mechanochemical or mechanical nature, with an organic agent such as those described for example in Cosmetics and Toiletries, February 1990, Vol. 105, pp. 53-64, before being dispersed in the composition in accordance with the disclosure. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example periluoroalkyl ethers; and fluorosilicone compounds.

The at least one surface-treated pigment that can be used in the cosmetic composition comprising the at least one hydrophobic film-forming polymer may also have been treated with a mixture of these compounds and/or may have undergone several surface treatments.

The at least one surface-treated pigment that can be useful in the context of the present disclosure may be prepared according to surface-treatment techniques that are well known to those skilled in the art, or may be commercially available in the required form.

For example, the at least one surface-treated pigment can be coated with an organic layer.

The organic agent with which the at least one pigment is treated may be deposited on the at least one pigment by evaporation of solvent, chemical reaction between the molecules of the surface agent or creation of a covalent bond between the surface agent and the at least one pigment.

The surface treatment may thus be performed, for example, by chemical reaction of a surface agent with the surface of the pigments and creation of a covalent bond between the surface agent and the at least one pigment or the fillers. This method is for example described in patent U.S. Pat. No. 4,578,266.

An organic agent covalently bonded to the at least one pigment may for instance be used.

The agent for the surface treatment may represent from 0.1% to 50% by weight, such as from 0.5% to 30% by weight and for example from 1% to 10% by weight, relative to the total weight of the at least one surface-treated pigment.

For example, the surface treatments of the at least one pigment may be chosen from the following treatments:

a PEG-silicone treatment, for instance the AQ surface treatment sold by LCW;

a chitosan treatment, for instance the CTS surface treatment sold by LCW;

a triethoxycaprylylsilane treatment, for instance the AS surface treatment sold by LCW;

a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a lauroyllysine treatment, for instance the LL surface treatment sold by LCW;

a lauroyllysine dimethicone treatment, for instance the LL/SI surface treatment sold by LCW;

a magnesium myristate treatment, for instance the MM surface treatment sold by LCW;

an aluminium dimyristate treatment, for instance the MI surface treatment sold by Miyoshi;

a perfluoropolymethylisopropyl ether treatment, for instance the FHC surface treatment sold by LCW;

an isostearyl sebacate treatment, for instance the HS surface treatment sold by Miyoshi;

a disodium stearoyl glutamate treatment, for instance the NAI surface treatment sold by Miyoshi;

a dimethicone/disodium stearoyl glutamate treatment, for instance the SA/NAI surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrogenosiloxane/perfluoroalkyl phosphate treatment, for instance the FS01 surface treatment sold by Daito;

a lauroyllysine/aluminium tristearate treatment, for instance the LL-AlSt surface treatment sold by Daito;

an octyltriethylsilane treatment, for instance the OTS surface treatment sold by Daito;

an octyltriethylsilane/perfluoroalkyl phosphate treatment, for instance the FOTS surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

a microcrystalline cellulose and carboxymethylcellulose treatment, for instance the AC surface treatment sold by Daito;

a cellulose treatment, for instance the C2 surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

The composition comprising the at least one hydrophobic film-forming polymer in accordance with the present disclosure may further comprise at least one surface-untreated pigment.

For example, the at least one pigment can be a nacre.

The at least one pigment may be present in an amount ranging from 0.5% to 40% by weight and for example from 1% to 20% by weight, relative to the total weight of the composition according to the disclosure.

According to the present disclosure, the ready-to-use composition and the cosmetic composition comprising the at least one hydrophobic film-forming polymer and the at least one pigment applied to the hair comprise at least one volatile solvent. In the context of the disclosure, the term "volatile solvent" means a compound that is liquid at room temperature (20° C.) and at atmospheric pressure, having a vapour pressure at 20° C. of greater than 0.1 mmHg, for example ranging from 0.1 to 300 mmHg and for instance ranging from 0.5 to 200 mmHg.

The at least one volatile solvent may be water, a non-silicone organic solvent or a silicone organic solvent, or mixtures thereof. Volatile non-silicone organic solvents that may be mentioned in a non-limiting manner include:

volatile C1-C4 alkanols such as ethanol or isopropanol;

volatile C5-C7 alkanes such as n-pentane, hexane, cyclopentane, 2,3-dimethylbutane, 2,2-dimethylbutane, 2-methylpentane or 3-methylpentane;

esters of liquid C1-C20 acids and of volatile C1-C8 alcohols such as methyl acetate, n-butyl acetate, ethyl acetate, propyl acetate, isopentyl acetate or ethyl 3-ethoxypropionate;

ketones that are liquid at room temperature and volatile, such as methyl ethyl ketone, methyl isobutyl ketone, diisobutyl ketone, isophorone, cyclohexanone or acetone;

volatile ethers such as dimethoxymethane, diethoxyethane or diethyl ether;

volatile glycol ethers such as 2-butoxyethanol, butyl diglycol, diethylene glycol monomethyl ether, propylene glycol n-butyl ether or propylene glycol monomethyl ether acetate;

volatile hydrocarbon-based oils such as volatile hydrocarbon-based oils containing from 8 to 16 carbon atoms, and mixtures thereof, and for example branched C8-C16 alkanes, for instance C8-C16 isoalkanes (also known as isoparaffins), isododecane, isodecane and, for example, the oils sold under the trade names ISOPAR or PERMETHYL, and mixtures thereof. Mention may also be made of isohexyl or isodecyl neopentanoate;

volatile C4-C10 perfluoroalkanes such as dodecafluoropentane, tetradecafluorohexane or decafluoropentane;

volatile perfluorocycloalkyls such as perfluoromethylcyclopentane, 1,3-perfluorodimethylcyclohexane and perfluorodecalin, sold, respectively, under the names FLUTEC PC1®, FLUTEC PC3® and FLUTEC PC6® by the company F2 Chemicals, and also perfluorodimethylcyclobutane and perfluoromorpholine;

the volatile fluoroalkyl or heterofluoroalkyl compounds corresponding to the following formula:

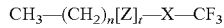

$CH_3—(CH_2)_n[Z]_t—X—CF_3$ in which t is 0 or 1; n is 0, 1, 2 or 3; X is a linear or branched divalent perfluoroalkyl radical containing from 2 to 5 carbon atoms, and Z represents O, S or NR, R is hydrogen or a radical $—(CH_2)_n—CH_3$ or $—(CF_2)_m—CF_3$, m is 2, 3, 4 or 5.

Among the volatile fluoroalkyl or heterofluoroalkyl compounds that may for example be mentioned are methoxynonafluorobutane sold under the names MSX 4518® and HFE-7100® by the company 3M, and ethoxynonafluorobutane sold under the name HFE-7200 by the company 3M.

For example, the at least one solvent can be chosen such that its boiling point is less than 200° C.

According to at least one embodiment, the non-silicone organic solvent is chosen from ethanol, isopropanol, acetone and isododecane.

Volatile silicone solvents that may be mentioned in a non-limiting manner include low-viscosity silicone compounds chosen from linear or cyclic silicones containing from 2 to 7 silicon atoms, these silicones optionally comprising alkyl or alkoxy groups containing from 1 to 10 carbon atoms, for example octamethylcyclotetrasiloxane, decamethylcyclopentasiloxane, dodecamethylcyclohexasiloxane, heptamethylhexyl-trisiloxane, heptamethylethyltrisiloxane, octamethyltrisiloxane and decamethyltetrasiloxane, and mixtures thereof. According to at least one embodiment, the silicone compound is chosen from cyclopentadimethylsiloxane, dodecamethylcyclohexasiloxane, octamethyltri-siloxane and decamethyltetrasiloxane.

Examples that may be further mentioned in a non-limiting manner include the decamethylcyclopentasiloxane sold under the name DC-245 by the company Dow Corning, the octamethyltrisiloxane sold under the name DC-200 FLUID 1 CST by the company Dow Corning, and the decamethyltetrasiloxane sold under the name DC-200 FLUID 1.5 CST by the company Dow Corning.

The at least one volatile solvent may be present in the ready-to-use cosmetic composition and in the composition comprising the at least one hydrophobic film-forming polymer and the at least one pigment in a content ranging from 0.1% to 95% by weight relative to the total weight of the composition, for example ranging from 1% to 90% by weight and for instance ranging from 5% to 90% by weight, relative to the total weight of the composition.

The ready-to-use cosmetic composition and the composition comprising the at least one hydrophobic film-forming polymer, the at least one pigment and the at least one volatile solvent in accordance with the disclosure may also comprise at least one other non-volatile organic solvent such as:

non-volatile aromatic alcohols such as benzyl alcohol or phenoxyethanol; esters of liquid C1-C20 acids and of non-volatile C1-C8 alcohols, such as isopropyl myristate;

thylene carbonate, propylene carbonate or butylene carbonate;

non-volatile polyols such as glycerol, ethylene glycol, dipropylene glycol or butylene glycol;

non-volatile glycol ethers, for instance diethylene glycol monomethyl ether or dipropylene glycol mono-n-butyl ether;

non-volatile hydrocarbon-based oils such as isohexadecane;

non-volatile liquid C10-C30 fatty alcohols such as oleyl alcohol; esters of liquid C10-C30 fatty alcohols such as benzoates of C10-C30 fatty alcohols and mixtures thereof; polybutene oil, isononyl isononanoate, isostearyl malate, pentaerythrityl tetraisostearate or tridecyl trimellitate; and non-volatile perfluoro solvents such as perfluoroperhydrophenanthrene, sold under the name FLUTEC PC11® by the company F2 Chemicals.

The ready-to-use cosmetic composition and the composition comprising the at least one hydrophobic film-forming polymer, the at least one pigment and the at least one volatile solvent may comprise at least one other colored or coloring species such as hydrophilic or hydrophobic direct dyes or dye precursors.

In order to obtain better spreading of the ready-to-use cosmetic composition and of the composition comprising the at least one hydrophobic film-forming polymer, the at least one pigment and the at least one volatile solvent in accordance with the disclosure and also improved coating, the compositions according to the present disclosure may also comprise at least one polysiloxane having a viscosity of greater than 100 cSt and for example greater than 300 cSt. The viscosity of the at least one polysiloxane may be measured according to ASTM standard D-445. The at least one polysiloxane may be chosen from silicone oils, gums or resins, and crosslinked silicones.

The at least one polysiloxane that may be present in the compositions according to the disclosure is different from the at least one hydrophobic film-forming polymer.

Moreover, the at least one polysiloxane that may be present in the compositions according to the disclosure is also different from the at least one volatile silicone solvent.

As polysiloxanes with a viscosity of greater than 100 cSt, mention may be made for example of polydimethylsiloxanes; alkyl dimethicones; polyphenylmethylsiloxanes such as phenyl dimethicones, phenyl trimethicones and vinyl methyl methicones; and also silicones modified with optionally fluorinated aliphatic and/or aromatic groups, or with functional groups such as hydroxyl, thiol and/or amine groups.

The at least one polysiloxane may be chosen from the silicones of formula (V):

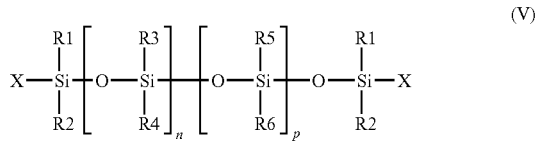

wherein:

R1, R2, R5, and R6 are, together or separately, an alkyl radical containing 1 to 6 carbon atoms, R3 and R4 are, together or separately, an alkyl radical containing from 1 to 6 carbon atoms, a vinyl radical, an aryl radical, an amine radical or a hydroxyl radical, X is an alkyl radical containing from 1 to 6 carbon atoms, a hydroxyl radical, a vinyl radical or an amine radical, n and p being integers chosen so as to obtain a viscosity of greater than 300 cSt.

Examples that may be mentioned include the following polydimethylsiloxanes:

the substituents R1 to R6 and X can represent a methyl group, such as the product sold under the name BAYSILICONE TP 3898 by the company General Electric, and the product sold under the name AK 500000 by the company Wacker, the substituents R1 to R6 and X can represent a methyl group, and p and n can be such that the molecular weight is 120,000 g/mol, such as the product sold under the name DOW CORNING 200 FLUID 60,000 CS by the company Dow Corning, the substituents R1 to R6 and X can represent a methyl group, and p and n can be such that the molecular weight is 250,000 g/mol, for instance the product sold under the name MIRASIL DM 500,000 by the company Rhodia and the product sold under the name DOW CORNING 200 FLUID 500,000 CST by the company Dow Corning, the substituents R1 to R6 can represent a methyl group, the group X can represent a hydroxyl group, and n and p can be such that the molecular weight of the polymer is 600,000 g/mol, for instance the product sold under the name SGM 36 by the company Dow Corning, dimethicones of the (polydimethylsiloxane)(methylvinylsiloxane) type, such as SE63 sold by GE Bayer Silicones, and poly(dimethylsiloxane)(diphenyl) (methylvinylsiloxane) copolymers, and mixtures thereof.

When the at least one polysiloxane comprises a fluoro group, it is possible to choose the copolymers having the following structure:

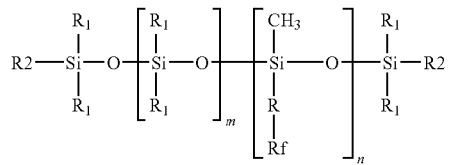

wherein:

R represents a linear or branched divalent alkyl group containing 1 to 6 carbon atoms, for instance a divalent methyl, ethyl, propyl or butyl group, Rf represents a fluoroalkyl radical, for instance a perfluoroalkyl radical, containing 1 to 12 carbon atoms and for example 1 to 9 carbon atoms, R1 represents, independently of each other, a $C_1$-$C_{20}$ alkyl radical, a hydroxyl radical or a phenyl radical, R2 represents R1 or Rf, m is chosen from 0 to 500 and for example from 0 to 200, and n is chosen from 1 to 1,000 and for example from 1 to 500.

For instance, in at least one embodiment, the groups R1 are identical and represent a methyl radical.

The at least one polysiloxane may be for example those sold by the company Shin-Etsu under the names FL-5, FL-10, X22-821 and X22-822 or FL-100 by the company Dow Corning, under the name FS-1265 FLUID by the company Phoenix Chemical, under the name PECOSIL FS or under the names PECOSIL FSL-150, PECOSIL FSL-300, PECOSIL FSH-150, PECOSIL FSH-300, PECOSIL FSU-150 and PECOSIL FSU-300.

The weight-average molecular mass of the at least one polysiloxane may range from 1,000 to 1,500,000 g/mol and for example from 20,000 to 1,000,000 g/mol.

The at least one polysiloxane may be in the form of resin. The term "resin" means a crosslinked or non-crosslinked three-dimensional structure. Examples of polysiloxane resins that may be mentioned include silsesquioxanes and siloxysilicates.

In at least one embodiment of the disclosure, the at least one polysiloxane that can be used in the composition of the disclosure is soluble or dispersible in the composition of the disclosure. In at least one embodiment, the at least one silicone resin is solid at 25° C.

The ready-to-use composition and the composition comprising the at least one hydrophobic film-forming polymer, the at least one pigment and the at least one volatile solvent in accordance with the disclosure may also comprise at least one crosslinked silicone such as a crosslinked elastomeric organopolysiloxane, a high molecular weight silicone compound of three-dimensional structure, having the viscoelastic properties of a supple solid material. These organopolysiloxanes may thus be in the form of dry powder, or in swollen form, in a solvent, the resulting product generally being a gel. These products may also be in dispersed form in an aqueous solution.

The synthesis of these organopolysiloxanes is described in the following documents: U.S. Pat. Nos. 5,266,321; 4,742,142; 5,654,362; and patent application FR 2 864 784.

The elastomeric organopolysiloxanes used in the composition may be partially or totally crosslinked. They are generally in the form of particles. For example, the elastomeric organopolysiloxane particles can have a number-average size ranging from 0.1 to 500 μm, for example from 3 to 200 μm and for instance from 3 to 50 μm. These particles may have any shape and may be, for example, spherical, flat, or amorphous.

The crosslinked organopolysiloxane obtained may be a non-emulsifying compound or an emulsifying compound. The term "non-emulsifying" defines crosslinked organopolysiloxanes not containing polyoxyalkylene units. The term "emulsifying" means crosslinked organopolysiloxane compounds having at least one polyoxyalkylene unit, for example polyoxyethylene or polyoxypropylene.

The crosslinked organopolysiloxane particles may be conveyed in the form of a gel constituted of a crosslinked organopolysiloxane included in at least one hydrocarbon-based oil and/or one silicone oil. In these gels, the organopolysiloxane particles may be non-spherical particles. The crosslinked organopolysiloxane particles may also be in the form of powder, such as in the form of spherical powder.

Non-emulsifying crosslinked organopolysiloxanes are for example described in patents U.S. Pat. Nos. 4,970,252, 4,987,169, 5,412,004, 5,654,362 and U.S. Pat. No. 5,760,116, and in patent application JP-A-61-194 009.

Non-emulsifying crosslinked organopolysiloxanes that may be used include those sold under the names KSG-6, KSG-15, KSG-16, KSG-18, KSG-31, KSG-32, KSG-33, KSG-41, KSG-42, KSG-43, KSG-44 and USG-103 by the company Shin-Etsu, DC9040, DC9041, DC9509, DC9505, DC9506 and DC9045 by the company Dow Corning, GRANSIL by the company Grant Industries, and SFE 839 by the company General Electric.

For example, the emulsifying crosslinked organopolysiloxanes may comprise polyoxyalkylene-modified organopolysiloxanes formed from divinyl compounds, for instance polysiloxanes containing at least two vinyl groups, which react with Si—H bonds of a polysiloxane. The emulsifying crosslinked organopolysiloxanes are for example described in patents U.S. Pat. Nos. 5,236,986, 5,412,004, 5,837,793 and U.S. Pat. No. 5,811,487.

The emulsifying crosslinked organopolysiloxanes that may be used include those sold under the names KSG-21, KSG-20, KSG-30 and X-226146 by the company Shin-Etsu, and DC9010 and DC9011 by the company Dow Corning.

The elastomeric crosslinked organopolysiloxane particles may also be in the form of a powder of elastomeric crosslinked organopolysiloxane coated with silicone resin, for instance with silsesquioxane resin, as described, for example, in patent U.S. Pat. No. 5,538,793.

Such elastomers are sold under the names KSP-100, KSP-101, KSP-102, KSP-103, KSP-104 and KSP-105 by the company Shin-Etsu.

When the at least one crosslinked silicone is present, the amount of the at least one crosslinked silicone may range from 0.1% to 30% by weight, for example from 0.1% to 20% by weight and for instance from 0.1% to 10% by weight.

The pretreatment composition and the cosmetic compositions comprising the at least one hydrophobic film-forming polymer may comprise at least one thickener chosen from polymeric thickeners other than the at least one hydrophobic film-forming polymer of the disclosure, and mineral thickeners, and mixtures thereof.

The at least one thickener may be mineral or organic, and polymeric or non-polymeric. The at least one thickener may be chosen to thicken an aqueous phase or a fatty phase of the composition, depending on the case.

The term "thickener" means a compound that modifies the rheology of the medium into which it is incorporated.

The at least one aqueous-medium thickener may be chosen from:
hydrophilic clays,
hydrophilic fumed silica,
water-soluble cellulose-based thickeners, such as hydroxyethylcellulose, methylcellulose or hydroxypropylcellulose. Among these, mention may be made for example of the gums sold under the name CELLOSIZE QP 4400H by the company Amerchol,
nonionic guar gums comprising $C_1$-$C_6$ hydroxyalkyl groups. Examples that may be mentioned include hydroxymethyl, hydroxypropyl and hydroxybutyl groups. Such guar gums are for example sold under the trade names JAGUAR HP8, JAGUAR HP60, JAGUAR HP120 and JAGUAR HP105 by the company Meyhall, or under the name GALACTASOL 40H4FD2 by the company Aqualon,
carrageenans,
locust bean gum, scleroglucan gum, gellan gum, rhamsan gum or karaya gum,
alginates, maltodextrins, starch and derivatives thereof, and hyaluronic acid and salts thereof,
the polyglyceryl (meth)acrylate polymers sold under the names HISPAGEL and LUBRAGEL by the companies Hispano Quimica or Guardian,
polyvinyl alcohol,
crosslinked acrylamide polymers and copolymers, such as those sold under the names PAS 5161 or BOZEPOL C by the company Hoechst, SEPIGEL 305 by the company SEPPIC, and SALCARE SC92 by the company Allied Colloid, or
the crosslinked methacryloyloxyethyltrimethylammonium chloride homopolymers sold under the name SALCARE SC95 by the company Allied Colloid,
associative polymers and for example associative polyurethanes.

Such thickeners are for example described in patent application EP-A-1 400 234.

The at least one oily-medium thickener may be chosen from:
organophilic clays;
hydrophobic fumed silicas;
alkyl guar gums (with a $C_1$-$C_6$ alkyl group), such as those described in EP-A-708 114;
oil-gelling polymers, for instance triblock polymers or star polymers resulting from the polymerization or copolymerization of at least one monomer containing an ethylenic group, for instance the polymers sold under the name KRATON;
polymers with a weight-average molecular mass of less than 100,000, comprising a) a polymer backbone comprising hydrocarbon-based repeating units containing at least one heteroatom, and optionally b) at least one pendent fatty chain and/or at least one terminal fatty chain, which are optionally functionalized, comprising from 6 to 120 carbon atoms and being linked to these hydrocarbon-based units, as described in patent applications WO-A-02/056847 and WO-A-02/47619; for example, polyamide resins (for instance comprising alkyl groups containing from 12 to 22 carbon atoms) such as those described in U.S. Pat. No. 5,783,657;
the silicone-based polyamide resins as described in patent application EP-A-1 266 647 and in the French patent application filed under the number 0 216 039.

Such thickeners are for example described in patent application EP-A-1 400 234.

The at least one thickener may be an organic gelling agent, i.e. an agent comprising at least one organic compound. The organogelling agents may be chosen from those described in patent application WO-A-03/105 788.

For example, the at least one polymeric thickener present in the composition according to the disclosure can be an amorphous polymer formed by polymerization of an olefin. The olefin may for instance be an elastomeric ethylenically unsaturated monomer.

Examples of olefins that may be mentioned include ethylenic carbide monomers, for example containing one or two ethylenic unsaturations, and containing from 2 to 5 carbon atoms, such as ethylene, propylene, butadiene, or isoprene.

The at least one polymeric thickener is capable of thickening or gelling the composition. The term "amorphous polymer" means a polymer that does not have a crystalline form. The at least one polymeric thickener may also be film-forming.

The at least one polymeric thickener may for example be a diblock, triblock, multiblock, radial or star copolymer, or mixtures thereof.

Such polymeric thickeners are described in patent application US-A-2002/005562 and in patent U.S. Pat. No. 5,221,534.

For instance, the at least one polymeric thickener can be an amorphous block copolymer of styrene and of olefin.

The at least one polymeric thickener for example may be hydrogenated to reduce the residual ethylenic unsaturations after the polymerization of the monomers.

For instance, the at least one polymeric thickener can be an optionally hydrogenated copolymer, comprising styrene blocks and ethylene/$C_3$-$C_4$ alkylene blocks.

Diblock copolymers, for example hydrogenated, that may be mentioned include styrene-ethylene/propylene copolymers and styrene-ethylene/butadiene copolymers. Diblock polymers are for example sold under the name KRATON® G1701E by the company Kraton Polymers.

Triblock copolymers, for example hydrogenated, that may be mentioned include styrene-ethylene/propylene-styrene copolymers, styrene-ethylene/butadiene-styrene copolymers, styrene-isoprene-styrene copolymers and styrene-butadiene-styrene copolymers. Triblock polymers are for example sold under the names KRATON® G1650, KRATON® G1652, KRATON® D1101, KRATON® D1102 and KRATON® D1160 by the company Kraton Polymers.

A mixture of styrene-butylene/ethylene-styrene triblock hydrogenated copolymer and of ethylene-propylene-styrene hydrogenated star polymer may also be used, such a mixture for example being in isododecane. Such mixtures are sold, for example, by the company Penreco under the trade names VERSAGEL® M5960 and VERSAGEL® M5670.

In at least one embodiment, a diblock copolymer such as those described previously, for example a styrene-ethylene/propylene diblock copolymer, is used as the at least one polymeric thickener.

For example, the organophilic clays can be clays modified with chemical compounds that make the clay capable of swelling.

Clays are products that are already well known per se, which are described, for example, in the book *Minéralogie des argiles* [Clay mineralogy], S. Caillère, S. Hénin, M. Rautureau, $2^{nd}$ edition 1982, Masson.

Clays are silicates containing a cation that may be chosen from calcium, magnesium, aluminium, sodium, potassium and lithium cations, and mixtures thereof.

Examples of such products that may be mentioned include clays of the smectite family such as montmorillonites, hectorites, bentonites, beidellites and saponites, and also of the family of vermiculites, stevensite and chlorites.

These clays may be of natural or synthetic origin. For example, clays that are cosmetically compatible and acceptable with keratin materials can be used.

The organophilic clay may be chosen from montmorillonite, bentonite, hectorite, attapulgite and sepiolite, and mixtures thereof. The clay can be for example a bentonite or a hectorite.

These clays may be modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned in a non-limiting manner include quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may be obtained by high-temperature hydrolysis of a volatile silicon compound in an oxhydric flame, producing a finely divided silica. This process makes it possible for example to obtain hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the said silica, via a chemical reaction generating a reduction in the number of silanol groups. It is for example possible to substitute silanol groups with hydrophobic groups: a hydrophobic silica can then be obtained.

The hydrophobic groups may be:
trimethylsiloxyl groups, which can be obtained for instance by treating fumed silica in the presence of hexamethyldisilazane. Silicas thus treated are known as "silica silylate" according to the CTFA (6th Edition, 1995). They are sold, for example, under the references AEROSIL R812® by the company Degussa and CAB-O-SIL TS-530® by the company Cabot;
dimethylsilyloxyl or polydimethylsiloxane groups, which can be obtained for example by treating fumed silica in the presence of polydimethylsiloxane or dimethyldichlorosilane. Silicas thus treated are known as "silica dimethyl silylate" according to the CTFA (6th Edition, 1995). They are sold, for example, under the references AEROSIL R972® and AEROSIL R974® by the company Degussa and CAB-O-SIL TS-610® and CAB-O-SIL TS-720® by the company Cabot.

The fumed silica for instance can have a particle size that may be nanometric to micrometric, for example ranging from about 5 to 200 nm.

An organomodified bentonite or hectorite may for example be used as mineral thickener.

The at least one thickener may be present in the composition in a total content ranging from 0.1% to 10% by weight, such as ranging from 0.5% to 7% by weight and for example ranging from 0.5% to 5% by weight, relative to the total weight of the composition comprising the at least one hydrophobic film-forming polymer.

The term "cosmetically acceptable medium" means a medium that is compatible with keratin fibers, such as the hair.

The cosmetically acceptable medium of the pretreatment composition according to the disclosure is formed from water, at least one cosmetically acceptable solvent or a mixture of water and of at least one cosmetically acceptable solvent. The at least one cosmetically acceptable solvent may be chosen from $C_1$-$C_4$ lower alcohols, such as ethanol or isopropanol, polyols and polyol ethers, for instance 2-butoxyethanol, propylene glycol, propylene glycol monomethyl ether, diethylene glycol monomethyl ether and monoethyl ether, and also aromatic alcohols, for instance benzyl alcohol or phenoxyethanol, and mixtures thereof.

For example, the cosmetically acceptable medium of the cosmetic pretreatment composition may be formed from water, from ethanol or from a mixture formed from water and ethanol.

The at least one organosilicon compound is soluble in the cosmetically acceptable medium and for example can be soluble to a concentration of 1%, such as to a concentration of 2% and for example to a concentration of 5% by weight in water at a temperature of 25° C.±5° C. and at atmospheric pressure. The term "soluble" means the formation of a single macroscopic phase.

The content of cosmetically acceptable medium in the cosmetic pretreatment composition may range from 0.1% to 99% by weight and for example from 5% to 98% by weight, relative to the total weight of the pretreatment composition.

The compositions according to the disclosure may also comprise at least one cosmetic adjuvant chosen, for example, from reducing agents, fatty substances, softeners, antifoams, moisturizers, UV-screening agents, mineral colloids, peptizers, solubilizers, fragrances, anionic, cationic, nonionic or amphoteric surfactants, proteins, vitamins, propellants, oxyethylenated or non-oxyethylenated waxes, paraffins, C10-C30 fatty acids such as stearic acid or lauric acid, and C10-C30 fatty amides such as lauric diethanolamide.

Each of the above additives may be present in an amount ranging from 0.01% to 20% by weight, relative to the weight of the composition.

A person skilled in the art will take care to select the at least one optional additive such that the beneficial properties intrinsically associated with the formation of the coating in accordance with the disclosure are not, or are not substantially, adversely affected.

The compositions in accordance with the disclosure may for example be in the form of a suspension, a dispersion, a solution, a gel, an emulsion, for instance an oil-in-water (O/W) or water-in-oil (W/O) emulsion, or a multiple emulsion (W/O/W or polyol/O/W or O/W/O), in the form of a cream, a mousse, a stick, a dispersion of vesicles, for example of ionic or nonionic lipids, a two-phase or multi-phase lotion, a spray, a powder or a paste. The composition may also be in the form of a lacquer.

A person skilled in the art can select the appropriate galenical form, and also the method for preparing it, on the basis of his general knowledge, taking into account firstly the nature of the constituents used, for example their solubility in the support, and secondly the intended use of the composition.

The present disclosure also relates to a cosmetic process for treating keratin fibers, such as the hair, which comprises applying an effective amount of the ready-to-use composition as described herein to the keratin fibers.

According to at least one embodiment, it is possible to mix extemporaneously, before application to the hair, the at least one suitably selected organosilicon compound, optionally dissolved in a volatile solvent, with a composition comprising at least one hydrophobic film-forming polymer, at least one pigment, and at least one volatile solvent.

The ready-to-use composition described above may be used on wet or dry hair, and also on any type of fair or dark, natural or dyed, permanent-waved, bleached or relaxed hair.

For instance, the ready-to-use composition according to the disclosure can be applied to wet hair.

According to at least one embodiment of the process of the disclosure, the hair is washed before application of the composition described above.

The application of the ready-to-use composition to the hair may be performed, for example, using a comb, a fine brush, a coarse brush, or the fingers.

The present disclosure also relates to a process for treating keratin fibers such as the hair, comprising applying, to the keratin fibers, a cosmetic pretreatment composition comprising, in a cosmetically acceptable medium, at least one organosilicon compound as defined herein, and applying, to the keratin fibers, a cosmetic composition comprising at least one hydrophobic film-forming polymer, at least one pigment, and at least one volatile solvent as defined herein.

For example, the treatment process comprises applying to the keratin fibers a cosmetic pretreatment composition comprising, in a cosmetically acceptable medium, at least one organosilicon compound as defined herein, optionally rinsing the fibers after an optional leave-in time, and optionally drying them, followed by applying a cosmetic composition comprising at least one hydrophobic film-forming polymer, at least one pigment, and at least one volatile solvent as defined herein.

The cosmetic compositions described above may be used on all types of hair: light or dark hair, natural hair or on hair that has undergone a cosmetic treatment such as permanent-waving, dyeing, bleaching, or relaxing.

The cosmetic pretreatment composition as described herein may be used on wet or dry hair. For example, the cosmetic pretreatment composition can be applied to clean hair.

For instance, the leave-on time between the pretreatment composition and the cosmetic composition comprising the at least one hydrophobic film-forming polymer may range from a few seconds to 60 minutes, such as from 30 seconds to 15 minutes and for example from 1 minute to 5 minutes.

The pretreatment composition may or may not be rinsed out before applying the composition comprising the at least one hydrophobic film-forming polymer.

For example, the pretreatment composition can be rinsed out, i.e. its application can be followed by a rinsing step.

The cosmetic composition comprising the at least one hydrophobic film-forming polymer, the at least one pigment, and the at least one volatile solvent may be used on wet or dry hair. The choice of the presence of the drying step depends on the at least one hydrophobic film-forming polymer used in the composition.

The application to the hair of the compositions described above may be performed, for example, using a comb, a fine brush, a coarse brush, or the fingers.

According to at least one embodiment, the application to keratin fibers of the ready-to-use composition or of the cosmetic composition comprising the at least one hydrophobic film-forming polymer is followed by drying the keratin fibers at a temperature above 40° C. According to at least one embodiment, this temperature is greater than 45° C. According to another embodiment, this temperature is greater than 45° C. and less than 220° C.

Drying may be performed immediately after the application or after a leave-on time that may range from 1 minute to 30 minutes.

For example, in addition to supplying heat, the hair may be dried using a flow of air. This flow of air during drying makes it possible to improve the individualization of the coating.

During drying, a mechanical action on the locks may be exerted, such as combing, brushing, or passing the fingers through.

The drying step of the process of the disclosure may be performed, for example, with a hood, a hairdryer, a smoothing iron, or a Climazon.

When the drying step is performed with a hood or a hairdryer, the drying temperature may range from 40 to 110° and for example from 50 to 90°.

When the drying step is performed with a smoothing iron, the drying temperature may range from 110 to 220° and for example from 140 to 200°.

Once the drying is complete, a final rinse or shampoo wash may optionally be performed.

The examples that follow serve to illustrate the present disclosure without being limiting in nature.

I. EXAMPLES OF READY-TO-USE COMPOSITIONS

Example 1

The following compositions were prepared:

0.6 g of Composition 1a was applied to a lock of 1 g of clean, wet permanent-waved hair. After a leave-on time of 2 minutes, the lock was dried with a hairdryer at a temperature of 80° C. for 2 minutes. This procedure was repeated for Compositions 1b, 1c, and 1d.

In each case, a colored lock having individualized hairs and shampoo-fast color was obtained.

Example 2

The following compositions were prepared:

| Composition | 2 inventive | 2b comparative |
| --- | --- | --- |
| 3-Aminopropyltriethoxysilane sold under the reference DOW CORNING Z-6011 SILANE by Dow Corning | 2 g | — |
| Dimethylpolysiloxane/urea copolymer sold under the reference WACKER-BELSIL ® UD 60 by Wacker | 10 g | 10 g |
| Polydimethylsiloxane sold by Dow Corning under the reference DOW CORNING 200 FLUID 60000 CS | 5 g | 5 g |
| Mica nacre coated with brown iron oxide sold by Eckart under the name PRESTIGE BRONZE | 10 g | 10 g |
| Isopropanol | 40 g | 40 g |
| Cyclopentadimethylsiloxane sold by Dow Corning under the name DC245 FLUID | qs 100 g | qs 100 g |

0.6 g of Composition 2 was applied to a lock of 1 g of clean, wet permanent-waved hair. After a leave-on time of 2 min-

| Composition | 1a | 1b | 1c | 1d |
| --- | --- | --- | --- | --- |
| 3-Aminopropyltriethoxysilane DOW CORNING Z-6011 SILANE (*) | 2 g | — | — | — |
| 3-Aminopropylmethyldiethoxysilane sold by Fluka under the reference 09309 | — | 2 g | — | — |
| N-(2-Aminoethyl)-3-aminopropyl-triethoxysilane sold by ABCR under the reference AB153226 | — | — | 2 g | — |
| Bis[3-triethoxysilylpropyl]amine sold by ABCR under the reference SIB1824.5 | — | — | — | 2 g |
| BioPSA 7-4405 (BioPSA 7-4400 40% diluted in isododecane) (*) | 20 g | 20 g | 20 g | 20 g |
| α,ω-Dihydroxylated polydimethylsiloxane/cyclopentadimethylsiloxane mixture (14.7/85.3) sold under the name DC1501 FLUID (*) | 10 g | 10 g | 10 g | 10 g |
| Polymethylsilsesquioxane sold under the name WACKER BELSIL PMS MK POWDER by the company Wacker | 3 g | 3 g | 3 g | 3 g |
| Mica nacre coated with brown iron oxide sold by Eckart under the name PRESTIGE BRONZE | 10 g | 10 g | 10 g | 10 g |
| Ethanol | 8 g | 8 g | 8 g | 8 g |
| Isododecane | qs 100 g | qs 100 g | qs 100 g | qs 100 g |

(*) sold by Dow Corning utes, the lock was dried with a hairdryer at a temperature of 80° C. for 2 minutes. A colored lock having individualized hairs and shampoo-fast color was obtained.

When Composition 2b was applied under the same conditions, the shampoo-fastness of the color was markedly inferior.

Example 3

The following compositions were prepared:

| Composition | 3 inventive | 3b comparative |
|---|---|---|
| N-(2-Aminoethyl)-3-aminopropyltriethoxysilane sold by ABCR under the reference AB153226 | 2 g | — |
| Acrylates/C12-22 alkyl methacrylate copolymer as a 48% dispersion in water sold by Rohm & Haas under the reference SOLTEX OPT | 20 g | 20 g |
| 7-3100 GUM BLEND HIP EMULSION sold by Dow Corning | 20 g | 20 g |
| Mica nacre coated with brown iron oxide sold by Eckart under the name PRESTIGE BRONZE | 10 g | 10 g |
| Lactic acid | pH 10 final | pH 10 final |
| Water | qs 100 g | qs 100 g |

0.6 g of Composition 3 was applied to a lock of 1 g of clean, wet permanent-dried hair. After a leave-on time of 2 minutes, the lock was dried with a hairdryer at a temperature of 80° C. for 2 minutes. A colored lock having individualized hairs and shampoo-fast color was obtained.

When Composition 3b was applied under the same conditions, the shampoo-fastness of the color was markedly inferior.

II. EXAMPLES OF PRETREATMENT COMPOSITIONS

Example 1

The following compositions were prepared:
Pretreatment Compositions 1:

| Composition | 1a | 1b | 1c |
|---|---|---|---|
| 3-Aminopropyltriethoxysilane DOW CORNING Z-6011 SILANE (*) | 10 g | — | — |
| 3-Aminopropylmethyldiethoxysilane sold by Fluka under the reference 09309 | — | 10 g | — |
| N-(2-Aminoethyl)-3-aminopropyl-triethoxysilane sold by ABCR under the reference AB153226 | — | — | 10 g |
| Lactic acid | pH 10 final | pH 10 final | pH 10 final |
| Water | qs 100 g | qs 100 g | qs 100 g |

Pretreatment Compositions 2:

| Composition | 2a | 2b | 2c | 2d |
|---|---|---|---|---|
| Bis[methyldiethoxysilyl-propyl]amine sold by ABCR under the reference SIB1620.0 | 2.5 g | — | 2.5 g | — |
| Bis[3-triethoxysilyl-propyl]amine sold by ABCR under the reference SIB1824.5 | — | 2.5 g | — | 2.5 g |
| Ethanol | 65 g | 65 g | qs 100 g | qs 100 g |
| Lactic acid | pH 10 final | — | pH 10 final | — |
| Acetic acid | — | pH 5 final | — | pH 5 final |
| Water | qs 100 g | qs 100 g | — | — |

Composition 3:

| Composition | 3 |
|---|---|
| BioPSA 7-4405 (BioPSA 7-4400 40% diluted in isododecane) (*) | 20 g |
| α,ω-Dihydroxylated polydimethylsiloxane/cyclopentadimethylsiloxane mixture (14.7/85.3) sold under the name DC1501 FLUID (*) | 10 g |
| Polymethylsilsesquioxane sold under the name WACKER BELSIL PMS MK POWDER by the company Wacker | 3 g |
| Mica nacre coated with brown iron oxide sold by Eckart under the name PRESTIGE BRONZE | 10 g |
| Disteardimonium hectorite (10%) and propylene carbonate (3%) in isododecane sold by Elementis under the name BENTONE GEL ISDV Isododecane | 15 g |
| Isododecane | qs 100 g |

(*) sold by Dow Corning 0.6 g of pretreatment Composition 1a was applied to a lock of 1 g of clean, dry permanent-waved hair. After a leave-on time of 5 minutes, the lock was rinsed. 0.6 g of composition 3 was then applied to the wet lock. After a leave-on time of 2 minutes, the lock was dried with a hairdryer at a temperature of 80° C. for 2 minutes. This procedure was repeated for pretreatment Compositions 1b, 1c, 2a, 2b, 2c, and 2d.

In each case, a colored lock having individualized hairs and shampoo-fast color was obtained.

Example 2

The following composition was prepared:
Composition 4

| Composition | 4 |
|---|---|
| Dimethylpolysiloxane/urea copolymer sold under the reference WACKER-BELSIL ® UD 60 by Wacker | 10 g |
| Polydimethylsiloxane sold by Dow Corning under the reference DOW CORNING 200 FLUID 60000 CS | 5 g |
| Mica nacre coated with brown iron oxide sold by Eckart under the name PRESTIGE BRONZE | 10 g |
| Isopropanol | 40 g |
| Cyclopentadimethylsiloxane sold by Dow Corning under the name DC245 FLUID | qs 100 g |

0.6 g of pretreatment Composition 1a of Example 1 was applied to a lock of 1 g of clean, wet permanent-waved hair. After a leave-on time of 5 minutes, the lock was rinsed and then dried with a hairdryer. 0.6 g of Composition 4 was then applied to the dry lock. After a leave-on time of 2 minutes, the lock was dried with a hairdryer at a temperature of 80° C. for 2 minutes. This procedure was repeated for pretreatment Compositions 1b and 1c of Example 1. In each case, a colored lock having individualized hairs and shampoo-fast color was obtained.

When only Composition 4 was applied, without the pretreatment, the shampoo-fastness of the color was markedly inferior.

Example 3

The following composition was prepared:
Composition 5

| | |
|---|---|
| Acrylates/C12-22 alkyl methacrylate copolymer as a 48% dispersion in water sold by Rohm & Haas under the reference SOLTEX OPT | 20 g |
| 7-3100 GUM BLEND HIP EMULSION sold by Dow Corning | 20 g |
| Lactic acid | pH 10 final |
| Mica nacre coated with brown iron oxide sold by Eckart under the name PRESTIGE BRONZE | 10 g |
| Water | qs 100 g |

0.6 g of pretreatment Composition 1a of Example 1 was applied to a lock of 1 g of clean, wet permanent-waved hair. After a leave-on time of 5 minutes, the lock was rinsed and then dried with a hairdryer. 0.6 g of Composition 5 was then applied to the dry lock. After a leave-on time of 2 minutes, the lock was dried with a hairdryer at a temperature of 80° C. for 2 minutes. This procedure was repeated for pretreatment Compositions 1b and 1c of Example 1. In each case, a colored lock having individualized hairs and shampoo-fast color was obtained.

When only Composition 5 was applied, without the pretreatment, the shampoo-fastness of the color was markedly inferior.

What is claimed is:

1. A cosmetic composition for treating keratin fibers, comprising:
    at least one organosilicon compound chosen from silanes comprising one, two and three silicon atoms, wherein the at least one organosilicon compound also comprises at least one basic chemical function and at least one group chosen from hydroxyl and hydrolysable groups per molecule;
    at least one hydrophobic film-forming polymer;
    at least one pigment; and
    at least one volatile solvent;
wherein the at least one organosilicon compound comprising one silicon atom is chosen from the compounds of formula (I):

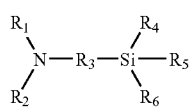

wherein:
    $R_4$ represents a halogen, a group OR', or $R'_1$;
    $R_5$ represents a halogen, a group OR'', or $R'_2$;
    $R_6$ represents a halogen, a group OR''', or $R'_3$;
    $R_1, R_2, R_3, R', R'', R''', R'_1, R'_2,$ and $R'_3$ represent, independently of each other, a saturated or unsaturated, linear or branched hydrocarbon-based group optionally bearing additional chemical groups, wherein $R_1, R_2, R', R'',$ and R''' also can be hydrogen, and at least two of the groups $R_4, R_5,$ and $R_6$ are different from the groups $R'_1, R'_2,$ and $R'_3$. and
wherein the at least one organosilicon compound comprising two or three silicon atoms is chosen from the compounds of formula (II):

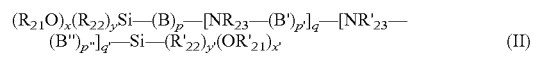

wherein:
    $R_{21}, R_{22}, R'_{21},$ and $R'_{22}$ each independently represent a saturated or unsaturated, linear or branched hydrocarbon-based chain, optionally comprising at least one heteroatom, optionally interrupted or substituted with at least one group chosen from ether, ester, amine, amide, carboxyl, hydroxyl, and carbonyl groups,
    x is an integer ranging from 1 to 3,
    y=3−x,
    x' is an integer ranging from 1 to 3,
    y'=3−x',
    p=0 or 1,
    p'=0 or 1,
    p''=0 or 1,
    q=0 or 1,
    q'=0 or 1,
    on the condition that at least q or q' is other than zero,
    B, B', and B'' each independently represent a linear or branched divalent $C_1$-$C_{20}$ alkylene radical,
    $R_{23}$ and $R'_{23}$ each independently represent a hydrogen atom or a saturated or unsaturated, linear or branched hydrocarbon-based chain, optionally comprising at least one heteroatom, optionally interrupted or substituted with at least one ether, ester of a $C_1$-$C_{20}$ alcohol, amine, carboxyl, alkoxysilane, $C_6$-$C_{30}$ aryl, hydroxyl or carbonyl groups, or a heterocyclic or non-heterocyclic aromatic ring, optionally substituted with at least one ester of a $C_3$-$C_{20}$ alcohol, amine, amide, carboxyl, alkoxysilane, hydroxyl, carbonyl or acyl groups.

2. The cosmetic composition according to claim 1, wherein the at least one basic chemical function of the at least one organosilicon compound is chosen from primary, secondary, and tertiary amine functions.

3. The cosmetic composition according to claim 1, wherein the at least one hydrolysable group is chosen from alkoxy, aryloxy, and halogen groups.

4. The cosmetic composition according to claim 1, wherein the groups $R_1, R_2, R', R'_1, R'_2, R'_3, R'',$ and R''' are chosen from $C_1$-$C_{12}$ alkyl radicals, $C_5$-$C_{14}$ aryl radicals, ($C_1$-$C_8$)alkyl($C_5$-$C_{14}$)aryl radicals and ($C_5$-$C_{14}$)aryl($C_1$-$C_8$)alkyl radicals, and the group $R_3$ is chosen from $C_1$-$C_{12}$ alkylene radicals, optionally substituted with an amino group, ($C_5$-$C_{14}$) arylene radicals, ($C_1$-$C_8$)alkylene($C_5$-$C_{14}$)arylene radicals and ($C_5$-$C_{14}$)arylene($C_1$-$C_8$)alkylene radicals.

5. The cosmetic composition according to claim 1, wherein the at least one organosilicon compound is chosen from 3-aminopropyltriethoxysilane, 3-aminopropylmethyldiethoxysilane, N-(2-aminoethyl)-3-aminopropyltriethoxysilane, and 3-(2-aminoethylamino)propylmethyldiethoxysilane.

6. The cosmetic composition according to claim 1, wherein the at least one hydrophobic film-forming polymer is chosen from polyurethanes; polyurethane-acrylics; polyureas; polyurea-polyurethanes; polyester-polyurethanes; polyether-polyurethanes; polyesters; polyester amides; acrylic polyesters; polyvinylpyrrolidone-based polymers or copolymers; acrylic and/or vinyl polymers or copolymers; polyacrylamides; silicone polymers comprising acrylic parts; silicone resins; polyurea/polyurethane silicones; copolymers based on silicone resin and dimethiconol; fluoro polymers; and celluloses.

7. The cosmetic composition according to claim 1, wherein the at least one volatile solvent is chosen from water and/or at least one organic solvent chosen from ethanol, isopropanol, acetone, isododecane, decamethylcyclopentasiloxane, octamethyltrisiloxane, and decamethyltetrasiloxane.

8. The cosmetic composition according to claim 1, wherein the at least one pigment is chosen from mineral pigments, organic pigments, lakes, and pigments with special effects.

9. The cosmetic composition according to claim 8, wherein the at least one pigment with special effects is chosen from nacres and glitter flakes.

10. The cosmetic composition according to claim 9, wherein the at least one pigment with special effects is chosen from nacres.

11. A process for treating keratin fibers, comprising
applying, to the keratin fibers, a cosmetic composition comprising
at least one organosilicon compound chosen from silanes comprising one, two and three silicon atoms, wherein the at least one organosilicon compound also comprises at least one basic chemical function and at least one group chosen from hydroxyl and hydrolysable groups per molecule;
at least one hydrophobic film-forming polymer;
at least one pigment; and
at least one volatile solvent; and
drying the keratin fibers at a temperature greater than 40° C;
wherein the at least one organosilicon compound comprising one silicon atom is chosen from the compounds of formula (I):

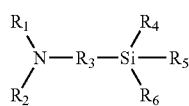

wherein:
$R_4$ represents a halogen, a group $OR'$, or $R'_1$;
$R_5$ represents a halogen, a group $OR''$, or $R'_2$;
$R_6$ represents a halogen, a group $OR'''$, or $R'_3$;
$R_1, R_2, R_3, R', R'', R''', R'_1, R'_2,$ and $R'_3$ represent, independently of each other, a saturated or unsaturated, linear or branched hydrocarbon-based group optionally bearing additional chemical groups, wherein $R_1, R_2, R', R'',$ and $R'''$ also can be hydrogen, and at least two of the groups $R_4, R_5,$ and $R_6$ are different from the groups $R'_1, R'_2,$ and $R'_3$; amd wherein the at least one organosilicon compound comprising two or three silicon atoms is chosen from the compounds of formula (II):

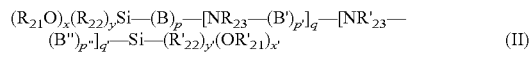

wherein:
$R_{21}, R_{22}, R'_{21},$ and $R'_{22}$ each independently represent a saturated or unsaturated, linear or branched hydrocarbon-based chain, optionally comprising at least one heteroatom, optionally interrupted or substituted with at least one group chosen from ether, ester, amine, amide, carboxyl, hydroxyl, and carbonyl groups, x is an integer ranging from 1 to 3,
y=3−x,
x' is an integer ranging from 1 to 3,
y'=3−x',
p=0 or 1,
p'=0 or 1,
p"=0 or 1,
q=0 or 1,
q'=0 or 1,
on the condition that at least q or q' is other than zero,
B, B', and B" each independently represent a linear or branched divalent $C_1$-$C_{20}$ alkylene radical,
$R_{23}$ and $R'_{23}$ each independently represent a hydrogen atom or a saturated or unsaturated, linear or branched hydrocarbon-based chain, optionally comprising at least one heteroatom, optionally interrupted or substituted with at least one ether, ester of a $C_1$-$C_{20}$ alcohol, amine, carboxyl, alkoxysilane, $C_6$-$C_{30}$ aryl, hydroxyl or carbonyl groups, or a heterocyclic or non-heterocyclic aromatic ring, optionally substituted with at least one ester of a $C_3$-$C_{20}$ alcohol, amine, amide, carboxyl, alkoxysilane, hydroxyl, carbonyl or acyl groups.

12. A method for making a composition for dyeing keratin fibers comprising
combining, in a cosmetically acceptable medium:
at least one organosilicon compound chosen from silanes comprising one, two and three silicon atoms, wherein the at least one organosilicon compound also comprises at least one basic chemical function and at least one group chosen from hydroxyl and hydrolysable groups per molecule;
at least one hydrophobic film-forming polymer;
at least one pigment; and
at least one volatile solvent
wherein the ingredients can be added in any order; and
wherein the at least one organosilicon compound comprising one silicon atom is chosen from the compounds of formula (I):

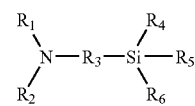

wherein:
$R_4$ represents a halogen, a group $OR'$, or $R'_1$;
$R_5$ represents a halogen, a group $OR''$, or $R'_2$;
$R_6$ represents a halogen, a group $OR'''$, or $R'_3$;
$R_1, R_2, R_3, R', R'', R''', R'_1, R'_2,$ and $R'_3$ represent, independently of each other, a saturated or unsaturated, linear or branched hydrocarbon-based group optionally bearing additional chemical groups, wherein $R_1, R_2, R', R'',$ and $R'''$ also can be hydrogen, and at least two of the groups $R_4, R_5,$ and $R_6$ are different from the groups $R'_1, R'_2,$ and $R'_3$; and wherein the at least one organosilicon compound comprising two or three silicon atoms is chosen from the compounds of formula (II):

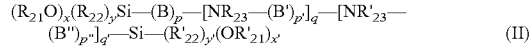

wherein:
$R_{21}, R_{22}, R'_{21},$ and $R'_{22}$ each independently represent a saturated or unsaturated, linear or branched hydrocarbon-based chain, optionally comprising at least one heteroatom, optionally interrupted or substituted with at least one group chosen from ether, ester, amine, amide, carboxyl, hydroxyl, and carbonyl groups, x is an integer ranging from 1 to 3,
y=3−x,
x' is an integer ranging from 1 to 3,
y'=3−x',
p=0 or 1,
p'=0 or 1,
p''=0 or 1,
q=0 or 1,
q'=0 or 1,
on the condition that at least q or q' is other than zero,
B, B', and B" each independently represent a linear or branched divalent $C_1$-$C_{20}$ alkylene radical,
$R_{23}$ and $R'_{23}$ each independently represent a hydrogen atom or a saturated or unsaturated, linear or branched hydrocarbon-based chain, optionally comprising at least one heteroatom, optionally interrupted or substituted with at least one ether, ester of a $C_1$-$C_{20}$ alcohol, amine, carboxyl, alkoxysilane, $C_6$-$C_{30}$ aryl, hydroxyl or carbonyl groups, or a heterocyclic or non-heterocyclic aromatic ring, optionally substituted with at least one ester of a $C_3$-$C_{20}$ alcohol, amine, amide, carboxyl, alkoxysilane, hydroxyl, carbonyl or acyl groups.

13. A process for treating keratin fibers, comprising
applying to the keratin fibers a cosmetic pretreatment composition comprising, in a cosmetically acceptable medium, at least one organosilicon compound chosen from silanes comprising one, two and three silicon atoms, wherein the at least one organosilicon compound also comprises at least one basic chemical function and at least one group chosen from hydroxyl and hydrolysable groups per molecule; and
applying to the keratin fibers a cosmetic composition comprising at least one hydrophobic film-forming polymer, at least one pigment, and at least one volatile solvent;
wherein the at least one organosilicon compound comprising one silicon atom is chosen from the compounds of formula (I):

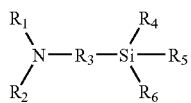
(I)

wherein:
$R_4$ represents a halogen, a group OR', or $R'_1$;
$R_5$ represents a halogen, a group OR", or $R'_2$;
$R_6$ represents a halogen, a group OR''', or $R'_3$;
$R_1$, $R_2$, $R_3$, R', R", R''', $R'_1$, $R'_2$, and $R'_3$ represent, independently of each other, a saturated or unsaturated, linear or branched hydrocarbon-based group optionally bearing additional chemical groups, wherein $R_1$, $R_2$, R', R", and R''' also can be hydrogen, and at least two of the groups $R_4$, $R_5$, and $R_6$ are different from the groups $R'_1$, $R'_2$, and $R'_3$; and wherein the at least one organosilicon compound comprising two or three silicon atoms is chosen from the compounds of formula (II):

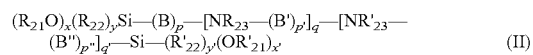
(II)

wherein:
$R_{21}$, $R_{22}$, $R'_{21}$, and $R'_{22}$ each independently represent a saturated or unsaturated, linear or branched hydrocarbon-based chain, optionally comprising at least one heteroatom, optionally interrupted or substituted with at least one group chosen from ether, ester, amine, amide, carboxyl, hydroxyl, and carbonyl groups, x is an integer ranging from 1 to 3,
y=3−x,
x' is an integer ranging from 1 to 3,
y'=3−x',
p=0 or 1,
p'=0 or 1,
p''=0 or 1,
q=0 or 1,
q'=0 or 1,
on the condition that at least q or q' is other than zero,
B, B', and B" each independently represent a linear or branched divalent $C_1$-$C_{20}$ alkylene radical,
$R_{23}$ and $R'_{23}$ each independently represent a hydrogen atom or a saturated or unsaturated, linear or branched hydrocarbon-based chain, optionally comprising at least one heteroatom, optionally interrupted or substituted with at least one ether, ester of a $C_1$-$C_{20}$ alcohol, amine, carboxyl, alkoxysilane, $C_6$-$C_{30}$ aryl, hydroxyl or carbonyl groups, or a heterocyclic or non-heterocyclic aromatic ring, optionally substituted with at least one ester of a $C_3$-$C_{20}$ alcohol, amine, amide, carboxyl, alkoxysilane, hydroxyl, carbonyl or acyl groups.

* * * * *

UNITED STATES PATENT AND TRADEMARK OFFICE
CERTIFICATE OF CORRECTION

PATENT NO. : 7,806,941 B2
APPLICATION NO. : 12/569287
DATED : October 5, 2010
INVENTOR(S) : Gaëlle Brun et al.

It is certified that error appears in the above-identified patent and that said Letters Patent is hereby corrected as shown below:

In claim 11, col. 43, line 54, "amd" should read --and--.

Signed and Sealed this

Seventh Day of December, 2010

David J. Kappos
*Director of the United States Patent and Trademark Office*